United States Patent [19]

Edwards et al.

[11] Patent Number: 5,217,964

[45] Date of Patent: Jun. 8, 1993

[54] POLYAMINE THIOLS AS RADIOPROTECTIVE AGENTS

[75] Inventors: Michael L. Edwards, Cincinnati; Ronald D. Snyder, Loveland, both of Ohio

[73] Assignee: Merrell Dow Pharmaceuticals Inc., Cincinnati, Ohio

[21] Appl. No.: 644,810

[22] Filed: Jan. 23, 1991

[51] Int. Cl.⁵ .................. A61K 31/66; A61K 31/135; C07F 9/165; C07C 211/14

[52] U.S. Cl. .................................... 514/104; 514/114; 514/654; 514/655; 558/158; 558/162; 558/166; 564/367; 564/368

[58] Field of Search ................ 564/368, 367; 558/158, 558/162; 514/654, 655, 104, 114

[56] References Cited

FOREIGN PATENT DOCUMENTS 0277635 8/1988 European Pat. Off. .
0311068 4/1989 European Pat. Off. .

OTHER PUBLICATIONS

T. R. Sweeney: A Survey of Compounds from the Antiradiation Drug Development Program of the U.S. Army Medical Research and Development Command. Walter Reed Army Institute of Research, Washington, D.C. (1979); pp. 517, 518, 743, 747, and 749.
J. Van Alphen: Rec. Trav. Chim. 58,544 (1939) and 59,31 (1940).
Weiss and Simic: Pharmac. Ther. 39,1 (1988).
Brown et al.: Pharmac. Ther. 39,157 (1988).
Grdina et al.: Pharmac. Ther. 39,21 (1988).

Primary Examiner—Mary C. Lee
Assistant Examiner—Michael G. Ambrose
Attorney, Agent, or Firm—Louis J. Wille

[57] ABSTRACT

The present invention relates to certain polyamine thiols which are useful as radioprotective agents.

18 Claims, No Drawings

POLYAMINE THIOLS AS RADIOPROTECTIVE AGENTS

BACKGROUND OF THE INVENTION

Radioprotective agents, also known as radioprotectors, are defined as agents which protect cells or organisms from deleterious cellular effects of exposure to ionizing radiation. These deleterious cellular effects include damage to cellular DNA, such as DNA strand break, disruption in cellular function, cell death, tumor induction and the like. The mechanism of this protective effect may at least partially be due to radical scavenging properties of the radioprotective agents.

The potential utility of these agents in protecting against exposure to environmental radiation, as well as in cancer radiation therapy, has long been recognized. These agents, administered prior to or during exposure, would eliminate or reduce the severity of deleterious cellular effects caused by exposure to environmental ionizing radiation such as resulting from a nuclear explosion, a spill of radioactive material, close proximity to radioactive material and the like.

In addition, these agents are believed to provide a selective protection of normal cells, and not of cancer cells, during cancer radiation therapy. For example, these agents, administered to the cancer patient prior to or during radiation therapy, will be absorbed by normal, non-cancer cells to provide a protective effect. However, the radioprotective agents will not be absorbed to the same extent by tumor cells due to the poor vascularity associated with the tumor. Therefore, the radioprotective agents would provide a selective protective effect on the normal cells as compared to tumor cells and would eliminate or reduce the severity of deleterious cellular effects of radiation therapy on normal cells. Furthermore, some radioprotective agents may act as prodrugs and require activation by cellular enzymatic processes which are not fully operative in the cancer cell. These agents, even if absorbed in a similar concentration in normal and cancer cells, will only be activated in cells with normal enzymatic processes and not in cancer cells. These prodrug radioprotective agents would be activated to provide a selective protective effect only in normal cells and would thus eliminate or reduce the severity of deleterious cellular effects of radiation therapy on normal cells.

Furthermore, certain radioprotective agents provide a selective protection against deleterious cellular effects in normal cells caused by certain DNA-reactive agents such as cisplatin, cyclophosphamide, diethylnitrosoamine, benzo(a)pyrene, carboplatin, doxorubicin, mitomycin-C and the like. Many of these DNA-reactive agents are chemotherapeutic agents useful in cancer therapy. Radioprotective agents are useful in eliminating or reducing the severity of deleterious effects in normal cells caused by exposure to these DNA-reactive agents, such as during cancer therapy with DNA-reactive chemotherapeutic agents.

In addition, certain radioprotective agents provide a selective protection against therapy-induced secondary tumor induction [See Grdina et al., Pharmac. Ther. 39, 21 (1988)]. Radiation and chemotherapy provide effective treatments for a variety of neoplastic disease states. Unfortunately, these treatments themselves are often-times mutagenic and/or carcinogenic and result in therapy-induced secondary tumor induction. For example, patients treated for Hodgkin's disease appear to exhibit a relatively high risk for therapy-induced acute myelogenous leukemia and non-Hodgkin's lymphoma. Radioprotective agents provide selective protection against deleterious cellular effects, such as tumor induction, caused by radiation therapy or chemotherapy with a DNA-reactive chemotherapeutic agent. Radioprotective agents are thus useful in eliminating or reducing the risk of secondary tumor induction brought about by radiotherapy or chemotherapy.

Radioprotective agents thus are useful in eliminating or reducing the severity of deleterious cellular effects in normal cells caused by environmental exposure to ionizing radiation, cancer radiation therapy and treatment with DNA-reactive chemotherapeutic agents. See generally, Weiss and Simic, Pharmac. Ther. 39, 1 (1988).

The prototypical radioprotective agent, developed by the Antiradiation Drug Development Program at the Walter Reed Army Institute of Research, is WR-2721, or S-2(3-aminopropylamino)ethylphosphorothioic acid, which has the structure

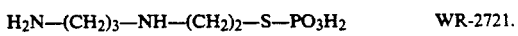

$$H_2N-(CH_2)_3-NH-(CH_2)_2-S-PO_3H_2 \quad \text{WR-2721.}$$

Other known radioprotective agents are WR-1065, thought to be a metabolite of WR-2721, which has the structure $$H_2N-(CH_2)_3-NH-(CH_2)_2-SH \quad \text{WR-1065,}$$

and WR-151,327, which has the structure $$CH_3NH-(CH_2)_3-NH-(CH_2)_3-SPO_3H_2 \quad \text{WR-151,327.}$$

SUMMARY OF THE INVENTION

The present invention provides novel radioprotective agents of the formula (1)

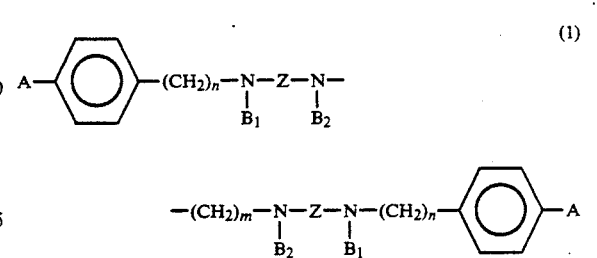

(1)

wherein
n is an integer from 0 to 3,
m is an integer from 4 to 9,
Z is a $C_2$-$C_6$ alkylene group,
A is H, —SH, —$SPO_3H_2$, —$N(CH_2)_q$—SH, —$N(CH_2)_q$—$SPO_3H_2$, wherein q is an integer 2 to 4, and
$B_1$ and $B_2$ are each independently H, —$(CH_2)_q$—SH, or —$(CH_2)_q$—$SPO_3H_2$,
with the proviso that at least one of A, $B_1$ and $B_2$ is other than H.

The present invention further provides novel radioprotective agents of the formula (2)

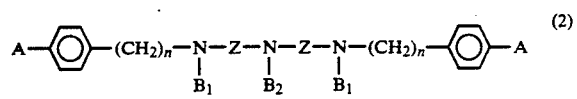

(2)

wherein
n is an integer from 0 to 3,

Z is a $C_2-C_6$ alkylene group,

A is H, $-SH$, $-SPO_3H_2$, $-N(CH_2)_q-SH$, $-N(CH_2)_q-SPO_3H_2$, wherein q is an integer 2 to 4, and $B_1$ and $B_2$ are each independently H, $-(CH_2)_q-SH$, or $-(CH_2)_q-SPO_3H_2$, with the proviso that at least one of A, $B_1$ and $B_2$ is other than H.

In addition, the present invention provides a method of protecting mammalian cells from deleterious cellular effects caused by exposure to ionizing radiation or to a DNA-reactive agent comprising contacting said cells with a protective amount of a compound of formula (1) or (2).

The present invention also provides a method of protecting non-cancer cells of a human from deleterious cellular effects caused by exposure to ionizing radiation or by exposure to a DNA-reactive agent comprising administering to said human a protective amount of a compound of formula (1) or (2).

The present invention further provides a method of treating a patient in need of radiation therapy, or in need of chemotherapy with a DNA-reactive chemotherapeutic agent, comprising administering to said patient a protective amount of a compound of formula (1) or (2).

DETAILED DESCRIPTION OF THE INVENTION

As used herein, the following terms have the meanings as indicated below:

1) The term "$C_2-C_6$ alkylene" refers to a saturated hydrocarbylene radical of from 2 to 6 carbon atoms of straight chain configuration. Specifically included within the scope of the term are the radicals $-CH_2CH_2-$, $-CH_2CH_2CH_2-$, $CH_2(CH_2)_2CH_2-$, $CH_2(CH_2)_3CH_2-$, $-CH_2(CH_2)_4CH_2-$;

2) The term "halo" or the term "Hal" refers to a chlorine, bromine or iodine atom;

3) The term "Pg" refers to a thiol protecting group such as S-methyl;

4) The term "Ms" refers to a mesylate functionality of the formula:

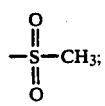

5) The term "Ts" refers to a tosylate functionality of the formula:

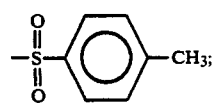

6) The term "Bz" refers to a benzoyl functionality of the formula:

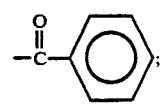

7) The term "BOC" refers to a t-butyloxycarbonyl functionality of the formula:

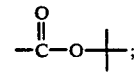

The compounds of formula (1) and (2) can be prepared according to standard procedures and techniques which are well known and appreciated in the art.

The compounds of formula (1) wherein $B_1$ is hydrogen and $B_2$ is $-(CH_2)_q-SH$ or $-(CH_2)_q-SPO_3H_2$, A is hydrogen and n=1, 2 or 3 can be prepared according to the general synthetic scheme set forth in Scheme A wherein all substituents, unless otherwise indicated, are previously defined.

Scheme A

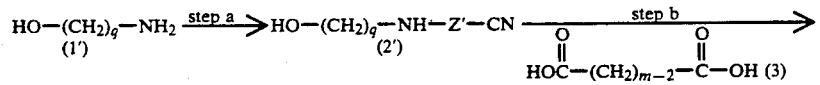

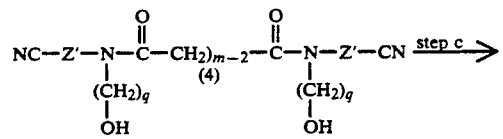

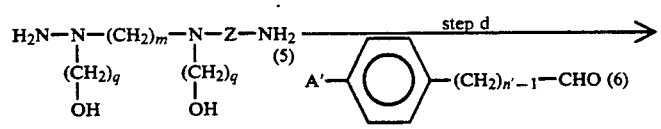

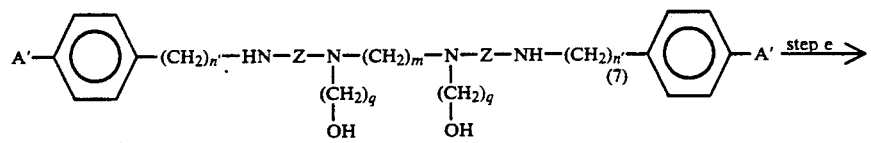

Scheme A -continued

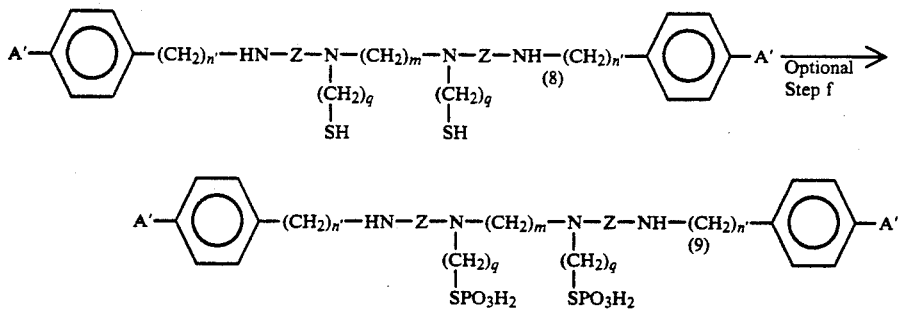

Z' = Z minus CH$_2$
A' = H
n' = 1, 2 or 3

In step a, the nitrogen functionality of an appropriate alkanolamine of structure (1') is alkylated to give the appropriate (hydroxyalkylamino)-alkylnitrile of structure (2'). Appropriate alkylating agents would be those which contain a nitrile functionality. For example, if the desired compound of formula (1) is one in which Z is represented by a C$_3$ alkylene group, an appropriate alkylating agent would be acrylonitrile. If the desired compound of formula (1) is one in which Z is represented by a C$_2$ or a C$_4$–C$_6$ alkylene group, appropriate alkylating agents would be the corresponding haloalkylnitriles.

For example, an appropriate alkanolamine of structure (1') is contacted with a molar equivalent of an appropriate alkylating agent. The reactants are typically contacted in a suitable protic organic solvent, such as ethanol. The reactants are typically stirred together for a period of time ranging from 5–24 hours and at a temperature range of from room temperature to reflux. The (hydroxyalkylamino)alkylnitrile of structure (2') is recovered from the reaction zone by evaporation of the solvent. It can be purified by distillation or silica gel chromatography.

In step b, the nitrogen functionality of the appropriate (hydroxyalkylamino)-alkylnitrile of structure (2') is amidated with an appropriate xdicarboxylic acid of structure (3) to give the appropriate N,N-bis(hydroxyalkyl)-N,N-bis(cyanoalkyl)dicarboxylic amide of structure (4).

For example, the appropriate (hydroxyalkylamino)alkylnitrile of structure (2') is contacted with one-half of a molar equivalent of the appropriate dicarboxylic acid of structure (3) and a molar equivalent of an amidating agent such as N-ethoxycarbonyl-2-ethoxy-1,2-dihydroquinoline (EEDQ). The reactants are typically contacted in a suitable organic solvent such as tetrahydrofuran. The reactants are typically stirred together for a period of time ranging from 2–24 hours and at a temperature range of from room temperature to reflux. The N,N-bis(hydroxyalkyl)-N,N-bis(cyanoalkyl)dicarboxylic amide of structure (4) is recovered from the reaction zone by evaporation of the solvent. It can be purified by silica gel chromatography.

In step c, both the nitrile and amide functionalities of the appropriate N,N-bis(hydroxyalkyl)-N,N-bis(cyanoalkyl)dicarboxylic amide of structure (4) are reduced to give the corresponding bis(hydroxyalkyl)tetraazaalkane of structure (5).

For example, the appropriate N,N-bis(hydroxyalkyl)-N,N-bis(cyanoalkyl)dicarboxylic amide of structure (4) is contacted with a molar excess of a reducing agent, such as lithium aluminum hydride. The reactants are typically contacted in a suitable organic solvent, such as ethyl ether. The reactants are typically stirred together at room temperature for a period of time ranging from 2–24 hours. The bis(hydroxyalkyl)-tetraazaalkane of structure (5) is recovered from the reaction zone by extractive methods as is known in the art. It can be purified by silica gel chromatography.

In step d, the terminal amino functionalities of the appropriate bis(hydroxyalkyl)-tetraazaalkane of structure (5) are reductively alkylated with the appropriate phenylalkylaldehyde of structure (6) to give the appropriate bis[(phenyl)alkyl]-bis(hydroxyalkyl)-tetraazaalkane of structure (7).

For example, the appropriate bis(hydroxyalkyl)tetraazaalkane of structure (5) is contacted with 2 molar equivalents of an appropriate phenylalkylaldehyde of structure (6), a molar excess of sodium cyanoborohydride and a catalytic amount of an acid-base indicator, such as bromocresol green. The reactants are typically contacted in a suitable protic organic solvent, such as ethanol. The reactants are typically stirred together while a suitable acid, such as hydrochloric acid, is added in order to maintain a slightly acidic medium as indicated by a yellow color. The reactants are typically stirred together at room temperature for a period of time necessary for the color to remain yellow. The bis[(phenyl)alkyl]-bis(hydroxyalkyl)tetraazaalkane of structure (7) is recovered from the reaction zone by extractive methods as is known in the art. It can be purified by silica gel chromatography.

In step e, hydroxy functionalities of the appropriate bis[(phenyl)alkyl]-bis(hydroxyalkyl)-tetraazaalkane of structure (7) are converted to the corresponding thiol functionalities to give the appropriate bis[(phenyl)alkyl]-bis(alkylthiol)-tetraazaalkane of structure (8).

For example, the appropriate bis[(phenyl)alkyl]-bis(hydroxyalkyl)-tetraazaalkane of structure (7) is contacted with a molar deficiency of phosphorus pentasulfide. The reactants are typically contacted in a suitable organic base, such as pyridine. The reactants are typically stirred together for a period of time ranging from 2–24 hours and at a temperature range from room temperature to reflux. The bis[(phenyl)alkyl]-bis(alkylthiol)-tetraazaalkane of structure (8) is recovered from the reaction zone by evaporation of the solvent. It can be purified by silica gel chromatography.

In optional step f, the thiol functionalities of the appropriate compound of formula (1) wherein A and B$_1$ are both hydrogen and B$_2$ is represented by —(CH$_2$-

$)_q$—SH (structure 8) may be converted to the corresponding phosphorothioates to give those compounds of formula (1) wherein A and B$_1$ are both hydrogen and B$_2$ is represented by —(CH$_2$)$_q$SPO$_3$H$_2$ (structure 9).

For example, the appropriate compound of formula (1) wherein A and B$_1$ are both hydrogen and B$_2$ is represented by —(CH$_2$)$_q$—SH (structure 8) is first contacted with 4 molar equivalents of triethyl phosphite and 2 molar equivalents of bromotrichloromethane. The reactants are typically stirred together for a period of time ranging from 1–3 hours and at a temperature range of from room temperature to reflux. The corresponding intermediate bis(diethylphosphorothioate) is recovered from the reaction zone by evaporation of the volatiles. It can be purified by silica gel chromatography.

The bis(diethylphosphonate) functionality of the intermediate bis(diethylphosphorothioate) is then cleaved to give the corresponding compound of formula (1) wherein A and B$_1$ are both hydrogen and B$_2$ is represented by —(CH$_2$)$_q$SPO$_3$H$_2$ (structure 9).

For example, the appropriate intermediate bis(diethylphosphorothioate) is contacted with a molar excess of trimethylsilyl bromide. The reactants are typically contacted in a suitable organic solvent such as methylene chloride. The reactants are typically stirred together for a period of time ranging from 2–24 hours and at a temperature range of from room temperature to reflux. The compound of formula (1) wherein A and B$_1$ are both hydrogen and B$_2$ is represented by —(CH$_2$)$_q$-SPO$_3$H$_2$ (structure 9) can be recovered from the reaction zone by evaporation of the solvent. It can be purified by silica gel chromatography.

Starting materials for use in the general synthetic procedures outlined in Scheme A are readily available to one of ordinary skill in the art.

The following example presents a typical synthesis as described in Scheme A. This example is understood to be illustrative only and is not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "μL" refers to microliters; "μg" refers to micrograms; and "μM" refers to micromolar.

EXAMPLE 1

1,19-Bis[(phenyl)methyl]-6,14-bis(ethanethiol)-1,6,14,19-tetraazanonadecane

Step a: 4N-(2-Hydroxyethylamino)butyronitrile

Dissolve ethanolamine (11.3 g, 0.185 mol) and 4-bromobutyronitrile (32.6 g, 0.22 mol) in ethanol (700 mL) and heat at reflux for 18 hours. Evaporate the solvent in vacuo and purify by distillation to give the title compound.

Step b:
N,N-Bis(2-hydroxyethyl)-N,N-bis(3-cyanopropyl)-pimelamide

Dissolve 4N-(2-hydroxyethylamino)butyronitrile (384 mg, 3 mmol) and pimelic acid (240 mg, 1.5 mmol) in tetrahydrofuran (25 mL). Add N-ethoxycarbonyl-2-ethoxy-1,2-dihydroquinoline (EEDQ) (791 mg, 3.2 mmol) and stir at room temperature for several hours. Evaporate the solvent in vacuo and purify by silica gel chromatography to give the title compound.

Step c:
6,14-Bis(2-hydroxyethyl)-1,6,14,19-tetraazanonadecane

Suspend lithium aluminum hydride (2.1 g, 0.054 mol) in ether (250 mL). Add, by dropwise addition, a solution of aluminum chloride (7.3 g, 0.054 mol) in ether (250 mL). Stir for 20 minutes and add a solution of N,N-bis(2-hydroxyethyl)-N,N-bis(3-cyanopropyl)-pimelamide (5.13 g, 0.0135 mol) in ether (25 mL). Stir at ambient temperature for 18 hours. Decompose the reducing agent by carefully adding water (20 mL) and 30% aqueous potassium hydroxide (100 mL). Filter and evaporate the solvent in vacuo and purify by silica gel chromatography to give the title compound.

Step d:
1,19-Bis[(phenyl)methyl]-1,19-bis(hydroxyethyl)-1,6,14,19-tetraazanonadecane Dissolve 6,14-bis(2-hydroxyethyl)-1,6,14,19-tetraazanonadecane (1.8 g, 0.005 mol) in methanol (distilled from Mg) (50 mL) and add benzadehyde (1.06 g, 0.01 mol), sodium cyanoborohydride (0.62 g, 0.010 mol) and 1 drop of 1% bromocresol green in ethanol. Maintain the pH of the reaction with 1N hydrochloric acid in methanol until the indicator no longer changes. Evaporate the solvent in vacuo and partition the residue between 1N sodium hydroxide (50 mL) and ethyl acetate (100 mL). Separate the organic phase, dry (MgSO$_4$) and evaporate the solvent in vacuo and purify by silica gel chromatography to give the title compound.

Step e:
1,19-Bis[(phenyl)methyl]-1,19-bis(ethanethiol)-1,6,14,19-tetraazanonadecane Dissolve 1,19-bis[(phenyl)methyl]-1,19-bis(hydroxyethyl)-1,6,14,19-tetraazanonadecane (1.10 g, 2.02 mmol) and phosphorus pentasulfinde (1 g, 4.5 mmol) in pyridine (30 mL). Reflux for several hours and pour into hot water (50 mL). Cool and extract into ethyl acetate. Dry (MgSO$_4$) and evaporate the solvent in vacuo . Purify by silica gel chromatography to give the title compound.

The following compounds can be prepared analogously to that described in Example 1:
1,19-Bis[(phenyl)methyl]-6,14-bis(ethanethiol)-1,6,14,19-tetraazanonadecane;
1,19-Bis[(phenyl)propyl]-6,14-bis(ethanethiol)-1,6,14,19-tetraazanonadecane;
1,17-Bis[(phenyl)methyl]-5,13-bis(ethanethiol)-1,5,13,17-tetraazanonadecane;
1,19-Bis[(phenyl)methyl]-6,14-bis(ethylphosphorothioate)-1,6,14,19-tetraazanonadecane.

The compounds of formula (1) wherein B$_1$ is —(CH$_2$)$_q$—SH or —(CH$_2$)$_q$—SPO$_3$H$_2$, B$_2$ is hydrogen, A is hydrogen and n=1, 2 or 3 can be prepared according to the general synthetic scheme set forth in Scheme B wherein all substituents, unless otherwise indicated, are previously defined.

Scheme B

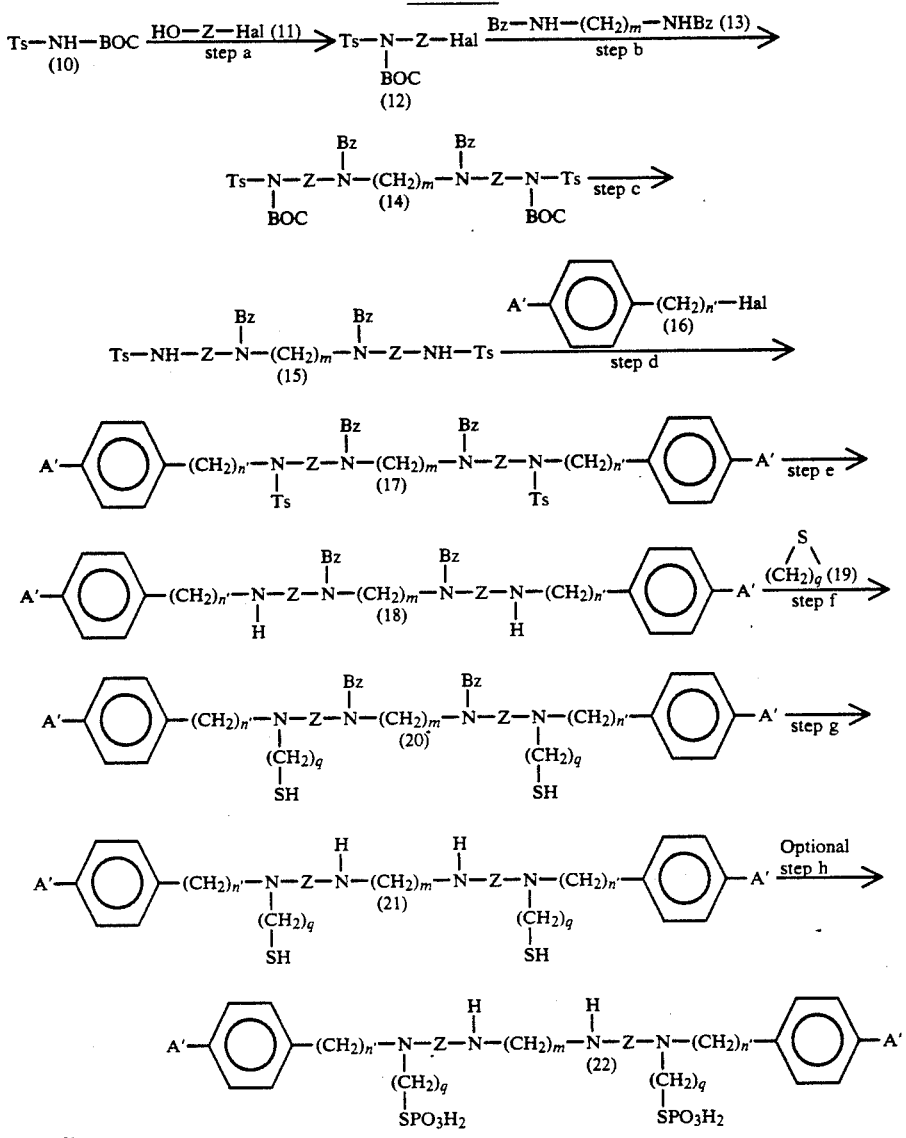

A' = H
n' = 1, 2 or 3

In step a, N-(t-butyloxycarbonyl)-N-[(4-methylphenyl)sulfonamide] (10) is alkylated with an appropriate haloalkanol of structure (11) to give the appropriate N-(t-butyloxycarbonyl)-N-[(4-methylphenyl)sulfonyl]-haloalkylamine of structure (12).

For example, N-(t-butyloxycarbonyl)-N-[(4-methylphenyl)sulfonamide](10) is contacted with a molar equivalent of triphenylphosphine, a molar equivalent of the appropriate haloalkanol of structure (11) and a molar equivalent of diethyl azodicarboxylate. The reactants are typically contacted in a suitable organic solvent such as tetrahydrofuran. The reactants are typically stirred together at room temperature for a period of time ranging from 2-24 hours. The N-(t-butyloxycarbonyl)-N-[(4-methylphenyl)sulfonyl]-haloalkylamine of structure (12) is recovered from the reaction zone by evaporation of the solvent. It can be purified by silica gel chromatography.

In step b, the alkyl halide functionality of the appropriate N-(t-butyloxycarbonyl)-N-[(4-methylphenyl)sulfonyl]-haloalkylamine of structure (12) is aminated with the appropriate bis(benzoyl)-diazaalkane of structure (13) to give the appropriate bis(t-butyloxycarbonyl)-bis[(4-methylphenyl)sulfonyl]-bis(benzoyl)-tetraazaalkane of structure (14).

For example, the appropriate bis(benzoyl)-diazaalkane of structure (13) is contacted with 2 molar equivalents of a non-nucleophilic base such as sodium hydride. The reactants are typically contacted in a suitable organic solvent such as dimethylformamide. The reactants are typically stirred together until evolution of hydrogen ceases at a temperature range of from 0° C. to room temperature. The appropriate N-(t-butyloxycarbonyl)-N-[(4-methylphenyl)sulfonyl]haloalkylamine of structure (12) is then added to the reaction mixture. The reactants are typically stirred together for a period of time ranging from 2-24 hours and at a temperature range of from 0° C. to 50° C. The bis(t-butyloxycarbonyl)-bis[(4-methylphenyl)sulfonyl]-bis(benzoyl)-tetraazaalkane of structure (14) is recovered from the reaction zone by extractive methods as is known in the art. It can be purified by silica gel chromatography.

In step c, the t-butyloxycarbonyl functionalities of the appropriate bis(t-butyloxycarbonyl)-bis[(4-methylphenyl)sulfonyl]-bis(benzoyl)-tetraazaalkane of structure (14) are hydrolyzed to give the appropriate bis[(4-methylphenyl)sulfonyl]-bis(benzoyl)-tetraazaalkane of structure (15).

For example, the appropriate bis(t-butyloxycarbonyl)bis[(4-methylphenyl)sulfonyl]-bis(benzoyl)-tetraazaalkane of structure (14) is contacted with a molar excess of an anhydrous acid, such as hydrochloric acid. The reactants are typically contacted in a suitable aprotic organic solvent, such as ethyl ether. The reactants are typically stirred together for a period of time ranging from 2–24 hours and at a temperature range of from 0° C. to room temperature. The bis[(4-methylphenyl)sulfonyl]-bis(benzoyl)-tetraazaalkane of structure (15) is recovered from the reaction zone by extractive methods as is known in the art. It can be purified by silica gel chromatography.

In step d, the bis[(4-methylphenyl)sulfonyl]functionalities of the appropriate bis[(4-methylphenyl)sulfonyl]-bis(benzoyl)-tetraazaalkane of structure (15) are alkylated with the appropriate phenylalkyl halide of structure (16) to give the bis[(phenyl)alkyl]-bis[(4-methylphenyl)sulfonyl]-bis(benzoyl)-tetraazaalkane of structure (17).

For example, the appropriate bis[(4-methylphenyl)sulfonyl]-bis(benzoyl)-tetraazaalkane of structure (15) is first contacted with 2 molar equivalents of an appropriate non-nucleophilic base such as sodium hydride. The reactants are typically contacted in a suitable organic solvent such as dimethylformamide. The reactants are typically stirred together at a temperature range of from 0° C. to room temperature until evolution of hydrogen ceases. An appropriate phenylalkyl halide of structure (16) is then added to the reaction mixture. The reactants are typically stirred together for a period of time ranging from 2–24 hours and at a temperature range of from room temperature to reflux. The bis[(phenyl)alkyl]-bis[(4-methylphenyl)sulfonyl]-bis(benzoyl)-tetraazaalkane of structure (17) is recovered from the reaction zone by extractive methods as is known in the art. It can be purified by silica gel chromatography.

In step e, the sulfonamide functionalities of the appropriate bis[(phenyl)alkyl]-bis[(4-methylphenyl)sulfonyl]-bis(benzoyl)-tetraazaalkane of structure (17) are cleaved to give the appropriate bis[(phenyl)alkyl]-bis(benzoyl)-tetraazaalkane of structure (18).

For example, the appropriate bis[(phenyl)alkyl]-bis[(4-methylphenyl)sulfonyl]-bis(benzoyl)-tetraazaalkane of structure (17) is contacted with a molar excess of sodium in liquid ammonia. The reactants are typically stirred together at a temperature range of from −60° C. to −20° C. for a period of time ranging from 1–10 hours. The bis[(phenyl)alkyl]-bis(benzoyl)-tetraazaalkane of structure (18) is recovered from the reaction zone by evaporation of the ammonia. It can be purified by silica gel chromatography.

In step f, the bis[(phenyl)alkyl]amine functionalities of the appropriate bis[(phenyl)alkyl]-bis(benzoyl)tetraazaalkane of structure (18) are alkylated with an appropriate thioalkylating agent of structure (19) to give the appropriate bis[(phenyl)alkyl]-bis(alkylthiol)bis(benzoyl)-tetraazaalkane of structure (20).

For example, the appropriate bis[(phenyl)alkyl]-bis(benzoyl)-tetraazaalkane of structure (18) is contacted with a molar excess of an appropriate thioalkylating agent of structure (19). The reactants are typically contacted in a suitable organic solvent, such as benzene. The reactants are typically stirred together for a period of time ranging from 2–10 hours and at a temperature range of from room temperature to reflux. The bis[(phenyl)alkyl]-bis(alkylthiol)-bis(benzoyl)-tetraazaalkane of structure (20) is recovered from the reaction zone by evaporation on the solvent. It can be purified by silica gel chromatography.

In step g, the bis(benzoyl) functionalities of the appropriate bis[(phenyl)alkyl]-bis(alkylthiol)-bis(benzoyl)tetraazaalkane of structure (20) are hydrolyzed to give the corresponding bis[(phenyl)alkyl]-bis(alkylthiol)tetraazaalkane of structure (21).

For example, the appropriate bis[(phenyl)alkyl]-bis(alkylthiol)-bis(benzoyl)-tetraazaalkane of structure (20) is contacted with a molar excess of an acid, such as hydrochloric acid. The reactants are typically stirred together for a period of time ranging from 2–24 hours at a temperature range of from room temperature to reflux. The bis[(phenyl)alkyl]-bis(alkylthiol)-tetraazaalkane of structure (21) is recovered from the reaction zone by extractive methods as is known in the art. It can be purified by silica gel chromatography.

In optional step h, the thiol functionalities of the appropriate compounds of formula (1) wherein A and $B_2$ are both hydrogen and $B_1$ is represented by —$(CH_2)_q$—SH (structure 21) may be converted to the corresponding phosphorothioates to give those compounds of formula (1) wherein A and $B_2$ are both hydrogen and $B_1$ is represented by —$(CH_2)_q SPO_3H_2$ (structure 22) as described previously in Scheme A, optional step f.

Starting materials for use in Scheme B are readily available to one of ordinary skill in the art. For example, N-(tert-butyloxycarbonyl)-N-[(4-methylphenyl)sulfonamide] is described in *Tetrahedron Lett.*, 30, 5709–12 1989.

The following example presents a typical synthesis as described in Scheme B. This example is illustrative only and is not intended to limit the scope of the present invention in any way.

EXAMPLE 2

1,19-Bis[(phenyl)methyl]-1,19-bis(ethanethiol)-1,6,14,19-tetraazanonadecane

Step a:
N-(tert-Butyloxycarbonyl)-N-[(4-methylphenyl)sulfonyl]-4-chlorobutylamine Dissolve N-(tert-butyloxycarbonyl)-N-[(4-methylphenyl)sulfonamide] (88 mg, 0.322 mmol) in anhydrous tetrahydrofuran (3 mL) and add triphenylphosphine (168 mg, 0.645 mmol). Stir under a nitrogen atmosphere and add 4-chloro-1-butanol (23.3 mg, 0.215 mmol) followed by diethyl azodicarboxylate (0.083 mL, 0.530 mmol). Stir at room temperature for several hours and evaporate the solvent in vacuo. Purify by silica gel chromatography to give the title compound.

Step b:
1,19-Bis(tert-Butyloxycarbonyl)-1,19-bis[(4-methylphenyl)sulfonyl]-6,14-bis(benzoyl)-1,6,14,19-tetraazanonadecane Dissolve 1,9-diazanonane (13 g, 0.1 mol) in pyridine (200 mL) and cool to 0° C. Add, by dropwise addition, benzoyl chloride (31 g, 0.22 mol) and stir overnight. Extract into chloroform, wash with water, 5% hydrochloric acid, 5% sodium hydroxide, water and dry (MgSO4). Evaporate the solvent in vacuo and purify by silica gel chromatography to give 1,9-bis(benzoyl)-1,9-diazanonane.

Suspend sodium hydride (4.8 g, 0.2 mol) in anhydrous dimethylformamide (100 mL), cool to 0° C. and place under a nitrogen atmosphere. Add, by dropwise addition, a solution 1,9-bis(benzoyl)-1,9-diazanonane (33.8 g, 0.1 mol) in dimethylformamide. Stir until evolution of hydrogen ceases. Add, by dropwise addition, a solution of N-(tert-butyloxycarbonyl)-N-[(4-methylphenyl)sulfonyl]-4-chlorobutylamine (72.4 g, 0.2 mol) in dimethylformamide (100 mL). Stir overnight at room temperature then carefully quench with saturated ammonium chloride. Extract into ethyl acetate, dry (MgSO4) and evaporate the solvent in vacuo. Purify by silica gel chromatogaphy to give the title compound.

Step c:
1,19-Bis[(4-methylphenyl)sulfonyl]-6,14-bis(benzoyl)-1,6,14,19-tetraazanonadecane Dissolve 1,19-Bis(tert-butyloxycarbonyl)-1,19-bis[(4-methylphenyl)sulfonyl]-6,14-bis(benzoyl)-1,6,14,19-tetraazanonadecane (9.76 g, 10 mmol) in saturated methanolic hydrochloric acid (100 mL). Stir for several hours and evaporate the solvent in vacuo. Dissolve the residue in water and neutralize with saturated sodium hydrogen carbonate and extract with ethyl acetate. Dry (MgSO4) and evaporate the solvent in vacuo. Purify by silica gel chromatography to give the title compound.

Step d:
1,19-Bis[(phenyl)methyl]-1,19-bis[(4-methylphenyl)sulfonyl]-6,14-bis(benzoyl)-1,6,14,19-tetraazanonadecane Suspend sodium hydride (48 mg, 2 mmol) in anhydrous dimethylformamide (2 mL), cool to 0° C. and place under a nitrogen atmosphere. Add, by dropwise addition, a solution 1,19-bis[(4-methylphenyl)sulfonyl]-6,14-bis(benzoyl)-1,6,14,19-tetraazanonadecane (78 mg, 1 mmol) in dimethylformamide (2 mL). Stir until evolution of hydrogen ceases. Add, by dropwise addition, a solution of benzylbromide (34 mg, 2 mmol) in dimethylformamide (2 mL). Stir overnight at room temperature then carefully quench with saturated ammonium chloride. Extract into ethyl acetate, dry (MgSO4) and evaporate the solvent in vacuo. Purify by silica gel chromatogaphy to give the title compound.

Step e:
1,19-Bis[(phenyl)methyl]-6,14-bis(benzoyl)-1,6,14,19-tetraazanonadecane

Mix 1,19-bis[(phenyl)methyl]-1,19-bis[(4-methylphenyl)sulfonyl]-6,14-bis(benzoyl)-1,6,14,19-tetraazanonadecane (4g, 4 mmol) in dry liquid ammonium (25 mL) at −40° C. Add small pieces of sodium until a permanent blue color remains. Discharge the excess sodium with saturated ammonium chloride. Allow the ammonia to evaporate spontaneously and partition the residue between ethyl acetate and water. Separate the organic phase, dry (MgSO4) and evaporate the solvent on vacuo. Purify by silica gel chromatography to give the title compound.

Step f:
1,19-Bis[(phenyl)methyl]-1,19-bis(ethanethiol)-6,14-bis(benzoyl)-1,6,14,19-tetraazanonadecane Dissolve 1,19-bis[(phenyl)methyl]-6,14-bis(benzoyl)-1,6,14,19-tetraazanonadecane (1.27 g, 1.92 mmol) in anhydrous benzene (20 mL). Add, by dropwise addition, a solution of ethylene sulfide (242 mg, 4 mmol) in anhydrous benzene (10 mL) over several hours at reflux. Reflux for an additional 2 hours, filter throught Celite and evaporate the solvent in vacuo. Purify the residue by silica gel chromatography.

Step g:
1,19-Bis[(phenyl)methyl]-1,19-bis(ethanethiol)-1,6,14,19-tetraazanonadecane Dissolve 1,19-Bis[(phenyl)methyl]-1,19-bis(ethanethiol)-6,14-bis(benzoyl)-1,6,14,19-tetraazanonadecane (7.8 g, 10 mmol) in 6N hydrochloric acid and heat at reflux for several hours. Cool to room temperature and carefully neutralize with saturated sodium hydrogen carbonate. Extract into ethyl acetate and dry (MgSO4). Evaporate the solvent in vacuo and purify the residue by silica gel chromatography to give the title compound.

The following compounds can be prepared analogously to that described in Example 2:
1,19-Bis[(phenyl)methyl]-1,19-bis(ethanethiol)-1,6,14,19-tetraazanonadecane;
1,19-Bis(phenyl)-1,19-bis(propanethiol)-1,6,14,19-tetraazanonadecane;
1,19-Bis[(phenyl)propyl]-1,19-bis(ethanethiol)-1,6,14,19-tetraazanonadecane;
1,19-Bis[(phenyl)methyl]-1,19-bis(propylphosphorothioate)-1,6,14,19-tetraazanonadecane.

The compounds of formula (1) wherein $B_1$ and $B_2$ are hydrogen, A is other than hydrogen and $n=1$, 2 or 3 can be prepared according to the general synthetic scheme set forth in Scheme C wherein all substituents, unless otherwise indicated, are previously defined.

Scheme C

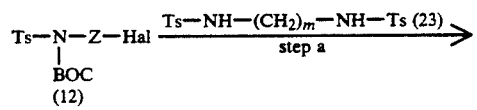

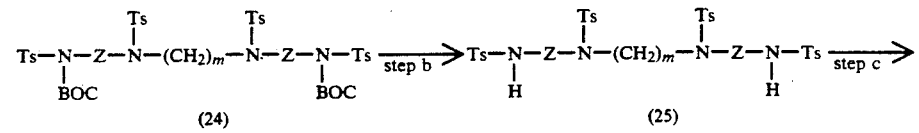

Scheme C -continued

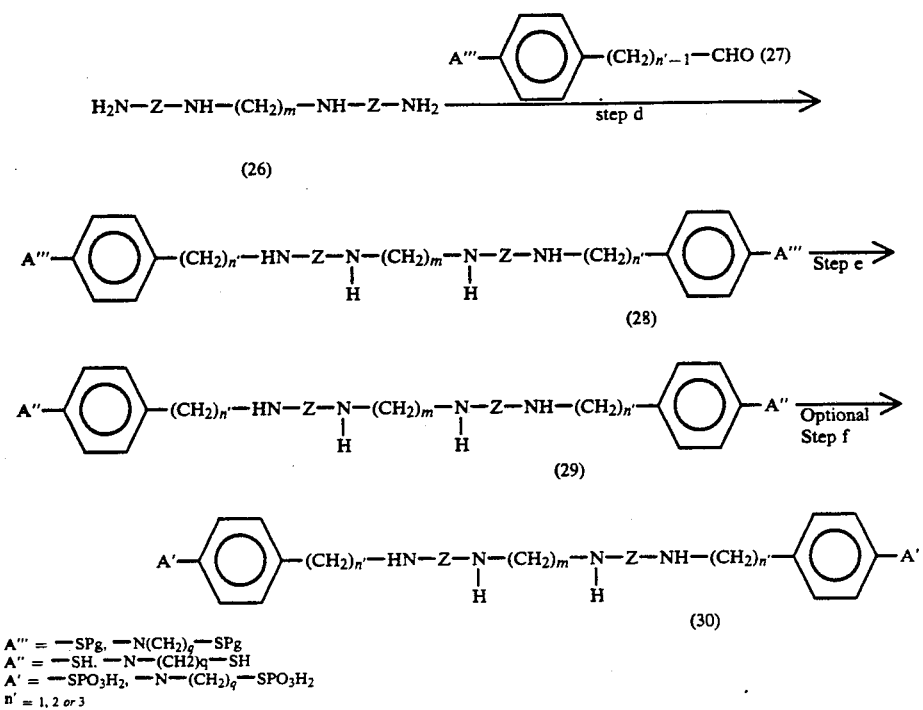

A''' = —SPg, —N(CH₂)$_q$—SPg
A'' = —SH, —N—(CH₂)q—SH
A' = —SPO₃H₂, —N—(CH₂)$_q$—SPO₃H₂
n' = 1, 2 or 3

In step a, the alkyl halide functionality of the appropriate N-(t-butyloxycarbonyl)-N-[(4-methylphenyl)sulfonyl]-haloalkylamine of structure (12) is aminated with the appropriate bis[(4-methylphenyl)sulfonyl]-diazaalkane of structure (23) to give the appropriate bis(t-butyloxycarbonyl)-tetra[(4-methylphenyl)sulfonyl]-tetraazaalkane of structure (24). Reaction conditions are similar to those described previously in Scheme B, step b.

In step b, the t-butyloxycarbonyl functionalities of the appropriate bis(t-butyloxycarbonyl)-tetra[(4-methylphenyl)sulfonyl]-tetraazaalkane of structure (24) are hydrolyzed to give the appropriate tetra[(4-methylphenyl)sulfonyl]-tetraazaalkane of structure (25) as described previously in Scheme B, step c.

In step c, the sulfonamide functionalities of the appropriate tetra[(4-methylphenyl)sulfonyl]-tetraazaalkane of structure (25) are cleaved to give the appropriate tetraazaalkane of structure (26) as described previously in Scheme B, step e.

In step d, the terminal amino functionalities of the appropriate tetraazaalkane of structure (26) are reductively alkylated with the appropriate thiol-protected (phenylthiol)-alkylaldehyde of structure (27) to give the appropriate thiol-protected bis[(phenyl)alkyl]-tetraazaalkane of structure (28) as described previously in Scheme A, step d.

The thiol functionality of the (phenylthiol)-alkylaldehyde of structure (27) must be protected due to the conditions of the reductive alkylation. The selection and utilization of appropriate thiol protecting groups are well known to one of ordinary skill in the art and are described in "Protective Groups in Organic Synthesis", Theodora W. Greene, Wiley (1981).

In step e, the protecting groups on the thiol functionalities of the appropriate thiol-protected bis[(phenyl)alkyl]-tetraazaalkane of structure (28) are removed to give the corresponding bis[(phenyl)alkyl]-tetraazaalkane of structure (29) by techniques and procedures well known and appreciated by one of ordinary skill in the art.

The bis[(phenyl)alkyl]-tetraazaalkane of structure 29) is purified by first converting the free amino functionalities to their corresponding t-butyloxycarbonamides with 4 molar equivaltents of di-t-butyldicarbonate. The reactants are typically contacted in a miscible organic solvent/aqueous base solvent mixture such as dioxane/sodium hydroxide. The reactants are typically stirred together at room temperature for a period of time ranging from 1-10 hours. The bis[(phenyl)alkyl]-bis(t-butyloxycarbonyl)-tetraazaalkane is recovered from the reaction zone by extractive methods as is known in the art. It can be purified by silica gel chromatography. The t-butyloxycarbonamide functionalities of the purified bis[(phenyl)alkyl]-bis(t-butyloxycarbonyl)-tetraazaalkane are then hydrolyzed with methanolic hydrochloric acid to give the purified bis[(phenyl)alkyl]-tetraazaalkane of structure (29) as its tetrahydrochloride salt.

In optional step f, the thiol functionalities of the appropriate compounds of formula (1) wherein A is a group represented by —SH or —N—(CH₂)$_q$—SH, B₁ and B₂ are both hydrogen and n=1, 2 or 3 (structure (29) may be converted to the corresponding phosphorothioates after deprotection to give those compounds of formula (1) wherein A is a group represented by —S-PO₃H₂ or —N—(CH₂)$_q$—SPO₃H₂, B₁ and B₂ are both represented by hydrogen and n=1, 2 or 3 (structure 30) as described previously in Scheme A, step f.

Starting materials for use in the general synthetic procedures outlined in Scheme C are readily available to one of ordinary skill in the art. For example, N-(tert-butyloxycarbonyl)-N-[(4-methylphenyl)sulfonamide] is described in *Tetrahedron Lett.*, 30, 5709-12 1989.

The following example presents a typical synthesis as described in Scheme C. This example is understood to be illustrative only and is not intended to limit the scope of the present invention in any way.

EXAMPLE 3

1,19-Bis[(4-mercaptophenyl)methyl -1,6,14,19-tetraazanonadecane, tetrahydrochloride Step a:
1,19-Bis(t-Butyloxycarbonyl)-1,6,14,19-tetra[(4-methylphenyl)sulfonyl]-1,6,14,19-tetraazanonadecane Dissolve 1,9-diazanonane (13 g, 0.1 mol) in pyridine (7.9 g, 0.10 mol) and cool to °C. Add, by dropwise addition, p-toluenesulfonyl chloride (41.9 g, 0.22 mol) and stir overnight. Extract into chloroform, wash with water, 5% hydrochloric acid, 5% sodium hydroxide, water and dry the organic phase (MgSO$_4$). Evaporate the solvent in vacuo and purify by silica gel chromatography to give 1,9-bis[(4-methylphenyl)sulfonyl]-1,9-diazanonane.

Suspend sodium hydride (4.8 g, 0.2 mol) in anhydrous dimethylformamide (100 mL), cool to 0° C. and place under a nitrogen atmosphere. Add, by dropwise addition, a solution 1,9-bis[(4-methylphenyl)sulfonyl]-1,9-diazanonane (43.8 g, 0.1 mol) in dimethylformamide. Stir until evolution of hydrogen ceases. Add, by dropwise addition, a solution of N-(t-butyloxycarbonyl)-N-[(4-methylphenyl)sulfonyl]-4-chlorobutylamine (72.4 g, 0.2 mol) in dimethylformamide (100 mL). Stir overnight at room temperature then carefully quench with saturated ammonium chloride. Extract into ethyl acetate, dry (MgSO$_4$) and evaporate the solvent in vacuo. Purify by silica gel chromatogaphy to give the title compound.

Step b:
1,6,14,19-Tetra[(4-methylphenyl)sulfonyl]-1,6,14,19-tetraazanonadecane Dissolve
1,19-bis(t-butyloxycarbonyl)-1,6,14,19-tetra[(4-methylphenyl)sulfonyl]-1,6,14,19-tetraazanonadecane (11.7 g, 10 mmol) in saturated methanolic hydrochloric acid (100 mL). Stir for several hours and evaporate the solvent in vacuo. Dissolve the residue in water and neutralize with saturated sodium hydrogen carbonate and extract with ethyl acetate. Dry (MgSO$_4$) and evaporate the solvent in vacuo. Purify by silica gel chromatography to give the title compound.

Step c: 1,6,14,19-Tetraazanonadecane

Mix 1,6,14,19-tetra[(4-methylphenyl)sulfonyl]-1,6,14,19-tetraazanonadecane (3.9 g, 4 mmol) in dry liquid ammonia (25 mL) at −40° C. Add small pieces of sodium until a permanent blue color remains. Discharge the excess sodium with saturated ammonium chloride. Allow the ammonia to evaporate spontaneously and partition the residue between ethyl acetate and water. Separate the organic phase, dry (MgSO$_4$) and evaporate the solvent in vacuo. Purify by silica gel chromatography to give the title compound.

Step d:
1,19-Bis[(4-methylmercaptophenyl)methyl]-1,6,14,19-tetraazanonadecane

Dissolve 1,6,14,19-tetraazanonadecane (1.35 g, 0.005 mol) in methanol (distilled from Mg) (50 mL) and add 4-(methylthio)benzaldehyde (1.52 g, 0.01 mol), sodium cyanoborohydride (0.62 g, 0.010 mol) and 1 drop of 1% bromocresol green in ethanol. Maintain the pH of the reaction with 1N hydrochloric acid in methanol until the indicator no longer changes. Evaporate the solvent in vacuo and partition the residue between 1N sodium hydroxide (50 mL) and ethyl acetate (100 mL). Separate the organic phase, dry (MgSO$_4$) and evaporate the solvent in vacuo give the title compound.

Step e:
1,19-Bis[(4-mercaptophenyl)methyl]-1,6,14,19-tetraazanonadecane

Dissolve 1,19-bis[(4-methylmercaptophenyl)methyl]-1,6,14,19-tetraazanonadecane (2.94 g, 5 mmol) in chloroform (20 mL) and treat with meta-chloroperbenzoic acid (863 mg, 5 mmol). Add calcium hydroxide (556 mg, 7.5 mmol) and stir for 15 minutes. Filter and evaporate the solvent in vacuo. Dissolve the residue in trifluoroacetic anhydride (10 mL) and heat at reflux for 30 minutes. Evaporate the volatiles in vacuo and dissolve the residue in a mixture of methanol-triethylamine (1:1, 100 mL) and evaporate the solvent in vacuo. Dissolve the residue in chloroform, wash with saturated ammonium chloride and dry (MgSO$_4$). Evaporate the solvent in vacuo to give the crude title compound.

Dissolve the crude 1,19-bis[(4-mercaptophenyl)methyl]-1,6,14,19-tetraazanonadecane (2.80 g, 5 mmol) in 50/50 dioxane/water (25 mL) and buffer to pH 10 with 1N sodium hydroxide. Add, by dropwise addition, an ether solution of di-t-butyl dicarbonate (4.8 g, 22 mmol) at 10° C. Allow to warm to room temperature and buffer occasionally to retain pH 10. Acidify with a sodium citrate/citric acid buffer to pH 5, extract with ether (3X), dry (MgSO$_4$) and evaporate the solvent in vacuo. Purify the residue by silica gel chromatography to give 1,19-bis[(4-mercaptophenyl)methyl]-1,6,14,19-tetra(t-butyloxycarbonyl)-1,6,14,19-tetraazanonadecane.

Dissolve 1,19-bis[(4-mercaptophenyl)methyl]-1,6,14,19-tetra(t-butyloxycarbonyl)-1,6,14,19-tetraazanonadecane (9.60 g, 10 mmol) in saturated methanolic hydrochloric acid (100 mL). Stir for several hours and evaporate the solvent in vacuo to give the title compound.

The following compound can be prepared analogously to that described in Example 3:

1,19-Bis[(4-(2-thioethylanilinyl)methyl -1,6,14,19-tetraazanonadecane;

1,12-Bis[(4-mercaptophenyl)methyl]-1,4,9,12-tetraazaundecane;

1,19-Bis[(4-mercaptophenyl)propyl]-1,5,13,19-tetraazanonadecane;

1,18-Bis[(4-mercaptophenyl)ethyl]-1,5,14,18-tetraazaoctadecane.

The compounds of formula (1) wherein B$_1$ and B$_2$ are hydrogen, A is other than hydrogen and n=0 can be prepared according to the general synthetic scheme set forth in Scheme D wherein all substituents, unless otherwise indicated, are previously defined.

Scheme D

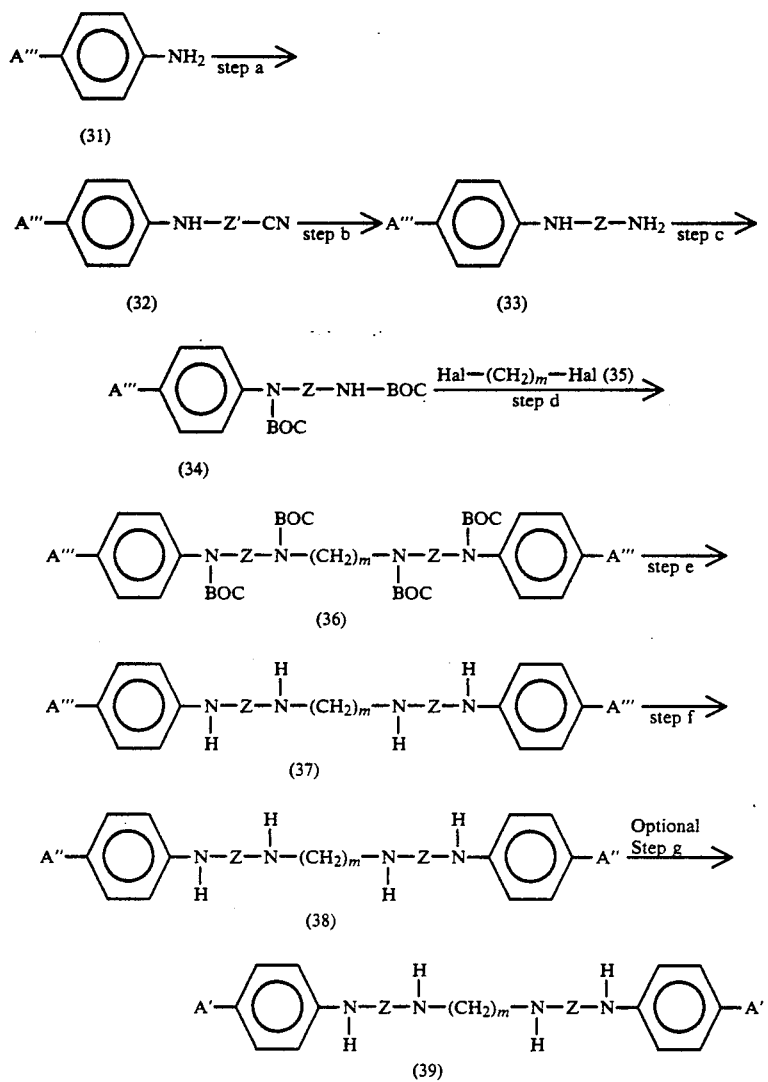

A''' = —SPg, —N(CH₂)$_q$—SPg
A'' = —SH, —N—(CH2)q—SH
A' = —SPO₃H₂, —N—(CH₂)$_q$—SPO₃H₂
Z' = Z minus CH2

In step a, the nitrogen functionality of an appropriate thiol-protected (mercapto)aniline of structure (31) is alkylated to give the appropriate thiol-protected N-alkylnitrile-(mercapto)aniline of structure (32) as described previously in Scheme A, step a.

In step b, the nitrile functionality of the appropriate thiol-protected N-alkylnitrile-(mercapto)aniline of structure (32) is reduced to give the thiol-protected N-(mercaptophenyl)-diazaalkane of structure (33) as described previously in Scheme A, step c.

In step c, the amino functionalities of the appropriate thiol-protected N-(mercaptophenyl)-diazaalkane of structure (33) are protected as the t-butyloxycarbonyl derivatives to give the corresponding thiol-protected N-(mercaptophenyl)bis(t-butyloxycarbonyl)-diazaalkane of structure (34).

For example, the appropriate thiol-protected N-(mercaptophenyl)-diazaalkane of structure (33) is contacted with 2 molar equivalents of an appropriate t-butyloxycarbonylating agent such as di-t-butyldicarbonate. The reactants are typically contacted in a miscible organic solvent/aqueous base mixture such as dioxane/sodium hydroxide. The reactants are typically stirred together at room temperature for a period of time ranging from 1-10 hours. The thiol-protected N-(mercaptophenyl)-bis(t-butyloxycarbonyl)-diazaalkane of structure (34) is recovered from the reaction zone by extractive methods as is known in the art. It can be purified by silica gel chromatography.

In step d, the terminal t-butyloxycarbamide functionality of the appropriate thiol-protected N-(mercaptophenyl)-bis(t-butyloxycarbonyl)-diazaalkane of structure (34) is alkylated with an appropriate dihaloalkane of structure (35) to give the thiol-protected bis(mercaptophenyl)-tetra(t-butyloxycarbonyl)-tetraazaalkane of structure (36).

For example, the appropriate thiol-protected N-(mercaptophenyl)-bis(t-butyloxycarbonyl)-diazaalkane (34) is contacted with 2 molar equivalents of a non-nucleophilic base such as sodium hydride. The reactants are typically contacted in a suitable organic solvent such as dimethylformamide. The reactants are typically stirred together until evolution of hydrogen ceases at a temperature range of from 0° C. to room temperature. The appropriate dihaloalkane of structure (35) is then added to the reaction mixture. The reactants are typically stirred together for a period of time ranging from 2-24 hours and at a temperature range of from 0° C. to room temperature. The thiol-protected bis(mercaptophenyl)-tetra(t-butyloxycarbonyl)-tetraazaalkane of structure (36) is recovered from the reaction zone by extractive methods as is known in the art. It can be purified by silica gel chromatography.

In step e, the t-butyloxycarbonamide functionalities of the appropriate thiol-protected bis(mercaptophenyl)-tetra(t-butyloxycarbonyl)-tetraazaalkane of structure (36) are hydrolyzed to give the corresponding thiol-protected bis(mercaptophenyl)-tetraazaalkane of structure (37) as described previously in Scheme B, step c.

In step f, the thiol-protecting groups of the appropriate thiol-protected bis(mercaptophenyl)tetraazaalkane of structure (37) are removed to give the corresponding bis(mercaptophenyl)-tetraazaalkane of structure (38) using techniques and procedures well known and appreciated by one of ordinary skill in the art.

In optional step g, the thiol functionalities of the appropriate compounds of formula (1) wherein A is a group represented by —SH or —N—$(CH_2)_q$—SH, $B_1$ and $B_2$ are both hydrogen and n=0 (structure 38) are both hydrogen may be converted to the corresponding phosphorothioates to give those compounds of formula (1) wherein A is a group represented by —$SPO_3H_2$ or —N—$(CH_2)_q$—$SPO_3H_2$, $B_1$ and $B_2$ are both represented by hydrogen and n=0 (structure 39) as described previously in Scheme A, optional step f.

Starting materials for use in Scheme D are readily available to one of ordinary skill in the art.

The following example presents a typical synthesis as described in Scheme D. This example is illustrative only and is not intended to limit the scope of the present invention in any way.

EXAMPLE 4

1,15-Bis(4-thiophenyl)-1,5,11,15-tetraazapentadecane

Step a: 3N-(4-methylthiophenyl)propionitrile

Dissolve 4-(methylmercapto)aniline (25.7 g, 0.185 mol) and acrylonitrile (11.7 g, 0.22 mol) in ethanol (700 mL) and heat at reflux for 18 hours. Evaporate the solvent in vacuo and purify by distillation to give the title compound.

Step b: 1-(4-methylthiophenyl)-1,5-diazapentane

Suspend lithium aluminum hydride (2.1 g, 0.054 mol) in ether (250 mL). Add, by dropwise addition, a solution of aluminum chloride (7.3 g, 0.054 mol) in ether (250 mL). Stir for 20 minutes and add a solution of 3N-(4-methylthiophenyl)propionitrile (10.4 g, 0.054 mol) in ether (25 mL). Stir at ambient temperature for 18 hours. Decompose the reducing agent by carefully adding water (20 mL) and 30% aqueous potassium hydroxide (100 mL). Filter and evaporate the solvent in vacuo and purify by silica gel chromatography to give the title compound.

Step c:
1-(4-methylthiophenyl)-1,5-bis(t-butyloxycarbonyl)1,5-diazapentane

Dissolve 1-(4-methylthiophenyl)-1,5-diazapentane (980 mg, 5 mmol) in 50/50 dioxane/water (25 mL) and buffer to pH 10 with 1N sodium hydroxide. Add, by dropwise addition, an ether solution of di-t-butyl dicarbonate (2.4 g, 11 mmol) at 10° C. Allow to warm to room temperature and buffer occasionally to retain pH 10. Acidify with a sodium citrate/citric acid buffer to pH 5, extract with ether (3X), dry (MgSO$_4$) and evaporate the solvent in vacuo. Purify the residue by silica gel chromatography to give the title compound.

Step d:
1,15-Bis(4-methylthiophenyl)-1,5,11,15-tetra(t-butyloxycarbonyl)-1,5,11,15-tetraazapentadecane Suspend sodium hydride (48 mg, 2 mmol) in anhydrous dimethylformamide (2 mL), cool to 0° C. and place under a nitrogen atmosphere. Add, by dropwise addition, a solution 1-(4-methylthiophenyl)-1,5-bis(t-butyloxycarbonyl)-1,5-diazapentane (1.58 g, 4 mmol) in dimethylformamide (2 mL). Stir until evolution of hydrogen ceases. Add, by dropwise addition, a solution of 1,5-dibromopentane (460 mg, 2 mmol) in dimethylformamide (2 mL). Stir overnight at room temperature then carefully quench with saturated ammonium chloride. Extract into ethyl acetate, dry (MgSO$_4$) and evaporate the solvent in vacuo. Purify by silica gel chromatogaphy to give the title compound.

Step e:
1,15-Bis(4-methylthiophenyl)-1,5,11,15-tetraazapentadecane

Dissolve 1,15-bis(4-methylthiophenyl)-1,5,11,15-tetra(t-butyloxycarbonyl)-1,5,11,15-tetraazapentadecanane (8.60 g, 10 mmol) in saturated methanolic hydrochloric acid (100 mL). Stir for several hours and evaporate the solvent in vacuo. Partition the residue between saturated sodium hydrogen carbonate and ethyl acetate. Separate the organic phase, dry (MgSO$_4$) and evaporate the solvent in vacuo to give the title compound.

Step f:
1,15-Bis(4-thiophenyl)-1,5,11,15-tetraazapentadecane

Dissolve 1,15-bis(4-methylthiophenyl)-1,5,11,15-tetraazapentadecane (2.3 g, 5 mmol) in chloroform (20 mL) and treat with meta-chloroperbenzoic acid (863 mg, 5 mmol). Add calcium hydroxide (556 mg, 7.5 mmol) and stir for 15 minutes. Filter and evaporate the solvent in vacuo. Dissolve the residue in trifluoroacetic anhydride (10 mL) and heat at reflux for 30 minutes. Evaporate the volatiles in vacuo and dissolve the residue in a mixture of methanol-triethylamine (1:1, 100 mL) and evaporate the solvent in vacuo. Dissolve the residue in chloroform, wash with saturated ammonium chloride and dry (MgSO$_4$). Evaporate the solvent in vacuo to give the title compound.

The following compounds may be prepared analogously to that described in Example 4:
1,12-Bis(4-thiophenyl)-1,4,9,12-tetraazadodecane;
1,19-Bis(4-thiophenyl)-1,5,13,19-tetraazanonadecane;
1,18-Bis(4-thiophenyl)-1,5,14,18-tetraazaoctadecane.

The compounds of formula (1) wherein $B_2$ and A are both hydrogen, $B_1$ is a group represented by —$(CH_2)_q$—SH or —$(CH_2)_q$—$SPO_3H_2$ and n=0 can be prepared according to the general synthetic scheme set forth in Scheme E wherein all substituents, unless otherwise indicated, are previously defined.

known in the art. It can be purified by silica gel chromatography.

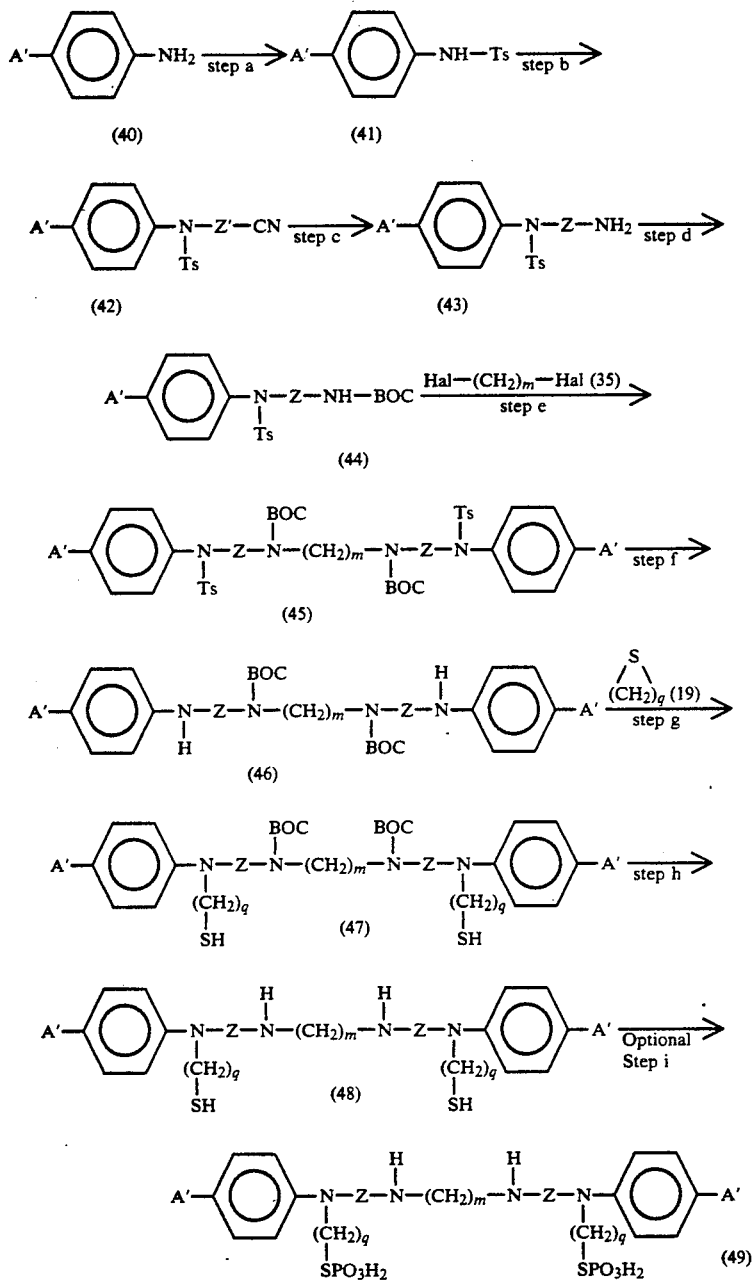

A' = H
Z' = Z minus CH$_2$

In step a, the appropriate aniline of structure (40) is converted to the corresponding N-[(4-methylphenyl)sulfonyl]aniline of structure (41).

For example, the appropriate aniline of structure (40) is contacted with a slight molar excess of p-toluenesulfonyl chloride. The reactants are typically contacted in an organic base such as anhydrous pyridine. The reactants are typically stirred together for a period of time ranging from 2-24 hours and at a temperature range of from 5° C. to room temperature. The N-[(4-methylphenyl)sulfonyl]aniline of structure (41) is recovered from the reaction zone by extractive methods as is In step b, the nitrogen functionality of an appropriate N-[(4-methylphenyl)sulfonyl]aniline of structure (41) is alkylated to give the appropriate N-alkylnitrile-N-[(4-methylphenyl)sulfonyl]aniline of structure (42) as described previously in Scheme A, step a.

In step c, the nitrile functionality of the appropriate N-alkylnitrile-N-[(4-methylphenyl)sulfonyl]aniline- of structure (42) is reduced to give the N-[(4-methylphenyl)sulfonyl]-N-phenyl-diazaalkane of structure (43) as described previously in Scheme A, step c.

In step d, the primary amino functionality of the appropriate N-[(4-methylphenyl)sulfonyl]-N-phenyldiazaalkane of structure (43) is protected as the t-butyloxycarbonyl derivative to give the corresponding N-[(4-methylphenyl)sulfonyl]-N-phenyl-N'-(t-butyloxycarbonyl)-diazaalkane of structure (44) as described previously in Scheme D, step c.

In step e, the terminal t-butyloxycarbamide functionality of the appropriate N-[(4-methylphenyl)sulfonyl]-N-phenyl-N'-(t-butyloxycarbonyl)diazaalkane of structure (44) is alkylated with an appropriate dihaloalkane of structure (35) to give the bis[(4-methylphenyl)sulfonyl]bis(phenyl)-bis(t-butyloxycarbonyl)-tetraazaalkane of structure (45) as described previously in Scheme D, step d.

In step f, the sulfonamide functionalities of the appropriate bis[(4-methylphenyl)sulfonyl]-bis(phenyl)-bis(t-butyloxycarbonyl)-tetraazaalkane of structure (45) are cleaved to give the appropriate bis(phenyl)-bis(t-butyloxycarbonyl)-tetraazaalkane of structure (46) as described previously in Scheme B, step e.

In step g, the terminal amine functionalities of the appropriate bis(phenyl)-bis(t-butyloxycarbonyl)tetraazaalkane of structure (46) are alkylated with an appropriate thioalkylating agent of structure (19) to give the appropriate bis(phenyl)-bis(alkylthiol)-bis(t-butyloxycarbonyl)-tetraazaalkane of structure (47) as described previously in Scheme B, step f.

In step h, the t-butyloxycarbonamide functionalities of the appropriate bis(phenyl)-bis(alkylthiol)-bis(t-butyloxycarbonyl)-tetraazaalkane of structure (47) are hydrolyzed to give the corresponding N,N-bis(phenyl)-N,N-bis(alkylthiol)-tetraazaalkane of structure (48) as described previously in Scheme B, step c.

In optional step i, the thiol functionalities of the appropriate Compounds of formula (1) wherein $B_1$ is a group represented by $-(CH_2)_q-SH$, A and $B_2$ are both hydrogen and $n=0$ (structure (48) may be converted to the corresponding phosphorothioates to give those compounds of formula (1) wherein $B_1$ is a group represented by $-(CH_2)_q-SPO_3H_2$, A and $B_2$ are both represented by hydrogen and $n=0$ (structure 49) as described previously in Scheme A, optional step f.

Starting materials for use in Scheme E are readily available to one of ordinary skill in the art.

The following example presents a typical synthesis as described in Scheme E. This example is illustrative only and is not intended to limit the scope of the present invention in any way.

EXAMPLE 5

1,15-Bis[(phenyl)]-1,15-bis(ethanethiol)-1,5,11,15-tetraazapentadecane, tetrahydrochloride Step a: N-[(4-Methylphenyl)sulfonyl]aniline Dissolve aniline (930 mg, 10 mmol) in anhydrous pyridine (25 mL) and cool to 5° C. Add, by dropwise addition, p-toluenesulfonyl chloride (2.1 g, 11 mmol) and stir overnight. Partition between water and ethyl acetate and separate the organic phase. Wash the organic phase with cold 1N hydrochloric acid, saturated sodium hydrogen carbonate and brine. Dry (MgSO$_4$) and evaporate the solvent in vacuo to give the title compound.

Step b:
N-Phenyl-N-[(4-methylphenyl)sulfonyl]-3-aminopropionitrile

Dissolve N-[(4-methylphenyl sulfonyl]aniline (45.7 g, 0.185 mol) and acrylonitrile (11.7 g, 0.22 mol) in ethanol (700 mL) and heat at reflux for 18 hours. Evaporate the solvent in vacuo and purify by distillation to give the title compound.

Step c:
1-Phenyl-1-[(4-methylphenyl)sulfonyl]-1,5-diazapentane

Suspend lithium aluminum hydride (2.1 g, 0.054 mol) in ether (250 mL). Add, by dropwise addition, a solution of aluminum chloride (7.3 g, 0.054 mol) in ether (250 mL). Stir for 20 minutes and add a solution of N-phenyl-N-[(4-methylphenyl)sulfonyl]-3-aminopropionitrile (16.2 g, 0.054 mol) in ether (25 mL). Stir at ambient temperature for 18 hours. Decompose the reducing agent by carefully adding water (20 mL) and 30% aqueous potassium hydroxide (100 mL). Filter and evaporate the solvent in vacuo and purify by silica gel chromatography to give the title compound.

Step d:
1-Phenyl-1-[(4-methylphenyl)sulfonyl]-5-(t-butyloxycarbonyl)-1,5-diazapentane Dissolve 1-phenyl-1-[(4-methylphenyl)sulfonyl]-1,5-diazapentane (1.52 g, 5 mmol) in 50/50 dioxane/water (25 mL) and buffer to pH 10 with 1N sodium hydroxide. Add, by dropwise addition, an ether solution of di-t-butyl dicarbonate (2.4 g, 11 mmol) at 10° C. Allow to warm to room temperature and buffer occasionally to retain pH 10. Acidify with a sodium citrate/citric acid buffer to pH 5, extract with ether (3X), dry (MgSO$_4$) and evaporate the solvent in vacuo. Purify the residue by silica gel chromatography to give the title compound.

Step e:
1,15-Bis[phenyl]-1,15-bis[(4-methylphenyl)sulfonyl]-5,11-bis(t-butyloxvcarbonyl)-1,5,11,15-tetraazapentadecane Suspend sodium hydride (48 mg, 2 mmol) in anhydrous dimethylformamide (2 mL), cool to 0° C. and place under a nitrogen atmosphere. Add, by dropwise addition, a solution of 1-phenyl-1-[(4-methylphenyl)sulfonyl]-5-(t-butyloxycarbonyl)-1,5-diazapentadecane (1.61 g, 4 mmol) in dimethylformamide (2 mL). Stir until evolution of hydrogen ceases. Add, by dropwise addition, a solution of 1,5-dibromopentane (460 mg, 2 mmol) in dimethylformamide (2 mL). Stir overnight at room temperature then carefully quench with saturated ammonium chloride. Extract into ethyl acetate, dry (MgSO$_4$) and evaporate the solvent in vacuo. Purify by silica gel chromatogaphy to give the title compound.

Step f:
1,15-Bis[phenyl]-5,11-bis(t-butyloxycarbonyl)-1,5,11,15-tetraazapentadecane Mix 1,15-bis[phenyl]-1,15-bis[(4-methylphenyl)sulfonyl]-5,11-bis(t-butyloxycarbonyl)-1,5,11,15-tetraazapentadecane (874 mg, 1 mmol) in dry liquid ammonia (25 mL) at $-40°$ C. Add small pieces of sodium until a permanent blue color remains.

Discharge the excess sodium with saturated ammonium chloride. Allow the ammonia to evaporate spontaneously and partition the residue between ethyl acetate and water. Separate the organic phase, dry (MgSO$_4$) and evaporate the solvent in vacuo. Purify by silica gel chromatography to give the title compound.

Step g:

1,15-Bis[phenyl]-1,15-bis(ethanethiol)-5,11-bis(t-butyloxycarbonyl)-1,5,11,15-tetraazapentadecane Dissolve 1,15-bis[phenyl]-1,15-bis(4-methylsulfonyl)-5,11-bis(t-butyloxycarbonyl)-1,5,11,15-tetraazapentadecane (1.09 g, 1.92 mmol) in anhydrous benzene (20 mL). Add, by dropwise addition, a solution of ethylene sulfide (242 mg, 4 mmol) in anhydrous benzene (10 mL) over several hours at reflux. Reflux for an additional 2 hours, filter throught Celite and evaporate the solvent in vacuo. Purify the residue by silica gel chromatography.

Step h:
1,15-Bis[(phenyl)]-1,15-bis(ethanethiol)-1,5,11,15-tetraazapentadecane, tetrahydrochloride Dissolve 1,15-bis[phenyl]-1,15-bis(ethanethiol)-5,11-bis(t-butyloxycarbonyl)-1,5,11,15-tetraazapentadecane (6.86 g, 10 mmol) in saturated methanolic hydrochloric acid (100 mL). Stir for several hours and evaporate the solvent in vacuo to give the title compound.

The following compounds may be prepared analogously to that described in Example 5:
1,19-Bis[(phenyl)]-1,19-bis(ethanethiol)-1,6,14,19-tetraazanonadecane, tetrahydrochloride;
1,17-Bis[(phenyl)]-1,17-bis(ethylphosphorothioate)-1,5,13,17-tetraazaheptadecane, tetrahydrochloride.

The compounds of formula (1) wherein $B_1$ and A are both hydrogen, $B_2$ is a group represented by —$(CH_2)_q$—SH or —$(CH_2)_q$—$SPO_3H_2$ and n=0 can be prepared according to the general synthetic scheme set forth in Scheme F wherein all substituents, unless otherwise indicated, are previously defined.

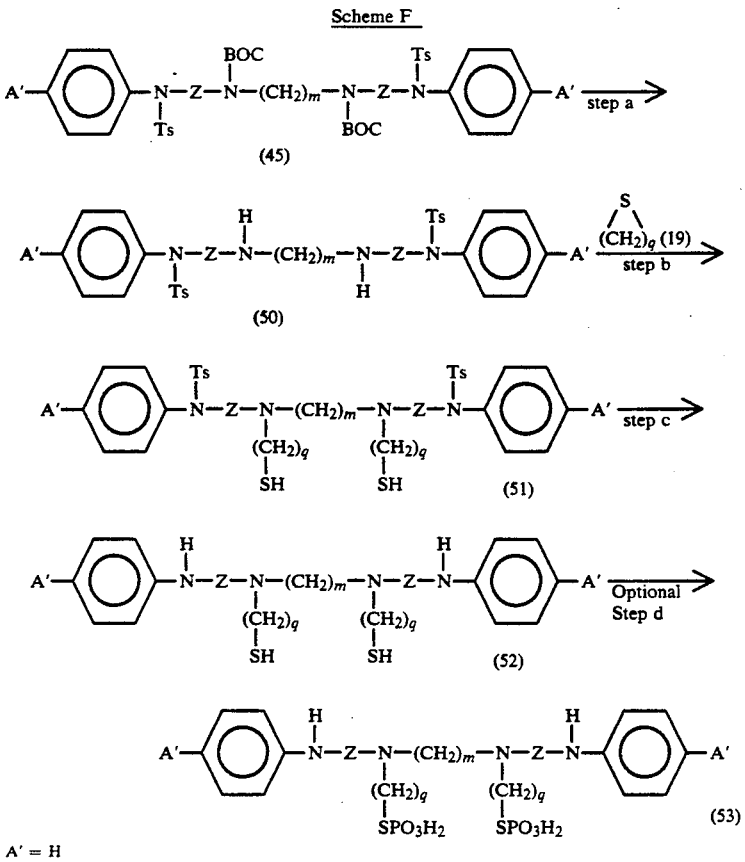

Scheme F $A' = H$

In step a, the t-butyloxycarbonamide functionalities of the appropriate bis[(4-methylphenyl)sulfonyl]-bis(phenyl)-bis(t-butyloxycarbonyl)-tetraazaalkane of structure (45) are hydrolyzed to give the corresponding bis[(4-methylphenyl)sulfonyl]-bis(phenyl)-tetraazaalkane of structure (50) as described previously in Scheme B, step c.

In step b, the bis(phenyl)amine functionalities of the appropriate bis[(4-methylphenyl)sulfonyl]-bis(phenyl)-tetraazaalkane of structure (50) are alkylated with an appropriate thioalkylating agent of structure (19) to give the appropriate bis(alkylthiol)-bis[(4-methylphenyl)sulfonyl]-tetraazaalkane of structure (51) as described previously in Scheme B, step f.

In step c, the sulfonamide functionalities of the appropriate bis(alkylthiol)-bis[(4-methylphenyl)sulfonyl]-tetraazaalkane of structure (51) are cleaved to give the appropriate bis(phenyl)-bis(ethanethiol)-tetraazaalkane of structure (52) as described previously in Scheme B, step e.

In optional step d, the thiol functionalities of the appropriate compounds of formula (1) wherein $B_2$ is a group -represented by —$(CH_2)_q$—SH, A and $B_1$ are both hydrogen and n=0 (structure 52) may be converted to the corresponding phosphorothioates to give those compounds of formula (1) wherein $B_2$ is a group represented by —$(CH_2)_q$—$SPO_3H_2$, A and $B_1$ are both represented by hydrogen and n=0 (structure 53) as described previously in Scheme A, optional step f.

Starting materials for use in Scheme F are readily available to one of ordinary skill in the art.

The following example presents a typical synthesis as described in Scheme F. This example is illustrative only and is not intended to limit the scope of the present invention in any way.

EXAMPLE 6

1,15-Bis[(phenyl)]-5,11-bis(ethanethiol)-1,5,11,15-tetraazapentadecane, tetrahydrochloride Step a:
1,15-Bis[(phenyl)]-1,15-bis[(4-methylphenyl)sulfonyl]-1,5,11,15-tetraazapentadecane Dissolve 1,15-bis[phenyl]-1,15-bis[(4-methylphenyl)sulfonyl]-5,11-bis(t-butyloxycarbonyl)-1,5,11,15-tetraazapentadecane (8.74 g, 10 mmol) in saturated methanolic hydrochloric acid (100 mL). Stir for several hours and evaporate the solvent in vacuo. Treat the residue carefully with saturated sodium hydrogen carbonate and extract into ethyl ether. Dry (MgSO$_4$) and evaporate the solvent in vacuo to give the title compound.

Step b:
1,15-Bis[phenyl]-5,11-bis(ethanethiol)-1,15-bis[(4-methylphenyl)sulfonyl]-1,5,11,15-tetraazapentadecane Dissolve 1,15-bis[(phenyl)]-1,15-bis[(4-methylphenyl)sulfonyl]-1,5,11,15-tetraazapentadecane (1.29 g, 1.92 mmol) in anhydrous benzene (20 mL). Add, by dropwise addition, a solution of ethylene sulfide (242 mg, 4 mmol) in anhydrous benzene (10 mL) over several hours at reflux. Reflux for an additional 2 hours, filter throught Celite and evaporate the solvent in vacuo. Purify the residue by silica gel chromatography.

Step c:
1,15-Bis[phenyl]-5,11-bis(ethanethiol)-1,5,11,15-tetraazapentadecane

Mix 1,15-bis[phenyl]-5,11-bis(ethanethiol)-1,15-bis[(4-methylphenyl)sulfonyl]-1,5,11,15-tetraazapentadecane (794 mg, 1 mmol) in dry liquid ammonium (25 mL) at −40° C. Add small pieces of sodium until a permanent blue color remains. Discharge the excess sodium with saturated ammonium chloride. Allow the ammonium to evaporate spontaneously and partition the residue between ethyl acetate and water. Separate the organic phase, dry (MgSO$_4$) and evaporate the solvent in vacuo. Purify by silica gel chromatography to give the title compound.

The following compounds may be prepared analogously to that described in Example 6:
1,19-Bis[(phenyl)]-6,14-bis(ethanethiol)-1,6,14,19-tetraazanonadecane, tetrahydrochloride;
1,17-Bis[(phenyl)]-5,13-bis(ethylphosphorothioate)-1,5,13,17-tetraazaheptadecane, tetrahydrochloride.

The compounds of formula (2) wherein $B_1$ and A are both hydrogen, $B_2$ is —(CH$_2$)$_q$—SH or —(CH$_2$)$_q$—S-PO$_3$H$_2$ and n=1, 2 or 3 can be prepared according to the general synthetic scheme set forth in Scheme G wherein all substituents, unless otherwise indicated, are previously defined.

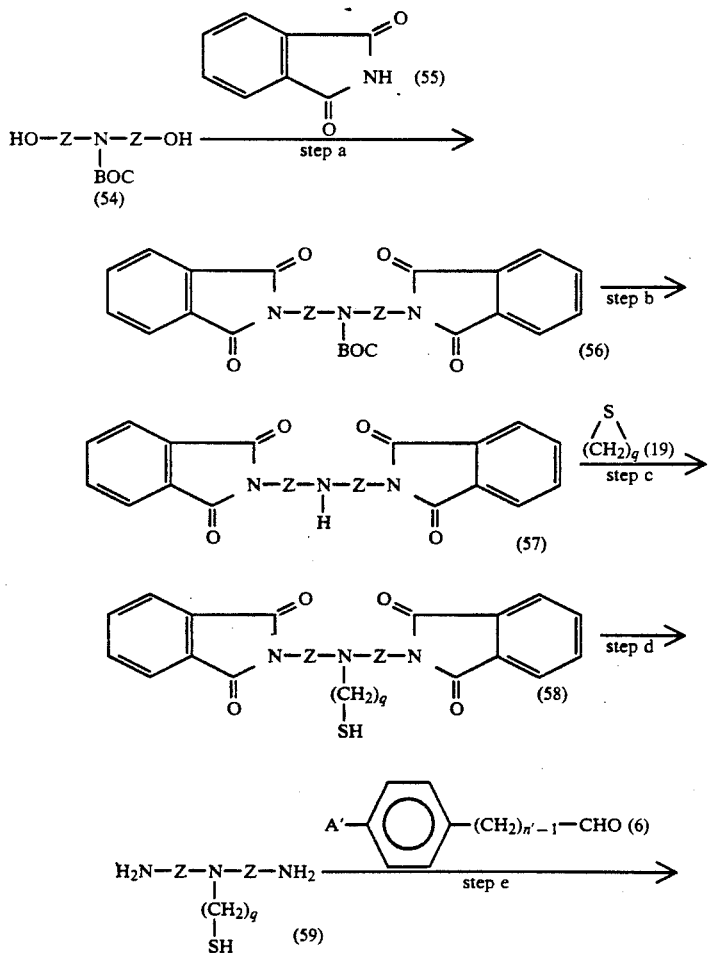

Scheme G
-continued

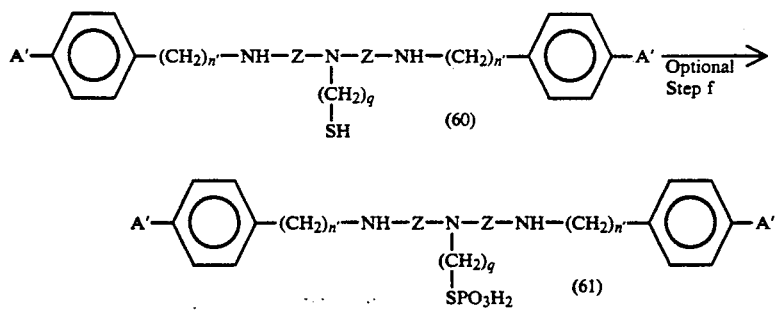

A' = H
n' = 1, 2 or 3

In step a, the appropriate bis(hydroxyalkyl)-t-butylcarboxamide of structure (54) is reacted with phthalimide (55) under Mitsunobu conditions to give the corresponding bis[(3-(1,3-dihydro-1,3-dioxo-2H-isoindol-2-yl)]-t-butyloxycarbamide of structure (56).

For example, the bis(hydroxyalkyl)-t-butyloxycarbamide of structure (54) is contacted with 2 molar equivalents of phthalimide (55), a molar equivalent of triphenylphosphine and a molar equivalent of diethyl azodicarboxylate. The reactants are typically contacted in a suitable organic solvent, such as tetrahydrofuran. The reactants are typically stirred together for a period of time ranging from 10 minutes to 5 hours. The bis[(3-(1,3-dihydro-1,3-dioxo-2H-isoindol-2-yl)]-t-butyloxycarbamide of structure (56) is recovered from the reaction zone by evaporation of the solvent. It can be purified by silica gel chromatography.

In step b, the t-butyloxycarbonyl functionality of the appropriate bis[(3-(1,3-dihydro-1,3-dioxo-2H-isoindol-2-yl)]-t-butyloxycarbamide of structure (56) is hydrolyzed to give the corresponding bis[3-(1,3-dihydro-1,3-dioxo-2H-isoindol-2-yl)]amine of structure (57) as described previously in Scheme B, step c.

In step c, the amine functionality of the appropriate bis[3-(1,3-dihydro-1,3-dioxo-2H-isoindol-2-yl)]amine of structure (57) is alkylated with an appropriate thioalkylating agent of structure (19) to give the corresponding bis[3-(1,3-dihydro-1,3-dioxo-2H-isoindol-2-yl)]-alkanethiolamine of structure (58) as described previously in Scheme B, step f.

In step d, the phthalimide functionalities of the appropriate bis[3-(1,3-dihydro-1,3-dioxo-2H-isoindol-2-yl)]-alkanethiolamine of structure (58) are removed to give the corresponding alkanethio-triazaalkane of structure (59).

For example, the appropriate bis[3-(1,3-dihydro-1,3-dioxo-2H-isoindol-2-yl)]-alkanethiolamine of structure (58) is contacted with 2 molar equivalents of hydrazine. The reactants are typically contacted in a suitable protic organic solvent such as methanol. The reactants are typically stirred together at reflux temperature for a period of time ranging from 2-24 hours. The alkanethio-triazaalkane of structure (59) is recovered from the reaction zone by extractive methods as is known in the art. It can be purified by silica gel chromatography.

In step e, the terminal amino functionalities of the appropriate alkanethio-triazaalkane of structure (59) are reductively aminated with the appropriate phenylalkylaldehyde of structure (6) to give the appropriate bis[(-phenyl)alkyl]-alkanethiol-triaazaalkane of structure (60) as described previously in Scheme A, step d.

In optional step f, the thiol functionality of the appropriate compounds of formula (2) wherein A and $B_1$ are both hydrogen, $B_2$ is represented by —$(CH_2)_q$—SH and n=1, 2 or 3 (structure 60) may be converted to the corresponding phosphorothioate to give those compounds of formula (2) wherein A and $B_1$ are both hydrogen, $B_2$ is represented by -$(CH_2)_q SPO_3H_2$ and n=1, 2 or 3 (structure 61) as described previously in Scheme A, optional step f.

Starting materials for use in the general synthetic procedures outlined in Scheme G are readily available to one of ordinary skill in the art.

The following example presents a typical synthesis as described in Scheme G. This example is illustrative only and is not intended to limit the scope of the invention in any way.

EXAMPLE 7

1,9-Bis[(phenyl)methyl]-5-ethanethiol-1,5,9-triazanonane

Step a:
Bis[3-(1,3-dihydro-1,3-dioxo-2H-isoindol-2-yl)]-t-butyloxycarbamide Dissolve bis(3-hydroxypropyl)amine (1.33 g, 10 mmol) in 50/50 dioxane/water (25 mL) and buffer to pH 10 with 1N sodium hydroxide. Add, by dropwise addition, an ether solution of t-butyl azidoformate (1.58 g, 11 mmol) at 10° C. Allow to warm to room temperature and buffer occasionally to retain pH 10. Acidify with a sodium citrate/citric acid buffer to pH 5, extract with ether (3×), dry (MgSO₄) and evaporate the solvent in vacuo. Purify the residue by silica gel chromatography to give bis(3-hydroxypropyl)-t-butyloxycarbamide.

Dissolve bis(3-hydroxypropyl)-t-butyloxycarbamide (410 mg, 1.76 mmol) in anhydrous tetrahydrofuran (5 mL). Add phthalimide (521 mg, 3.52 mmol), triphenylphosphine (929 mg, 3.52 mmol) and diethyl azodicarboxylate (613 mg, 3.52 mmol) at 0° C. Stir the mixture for 10 minutes at room temperature then evaporate the solvent in vacuo. Purify the residue by silica gel chromatography to give the title compound.

Step b:
Bis[3-(1,3-dihydro-1,3-dioxo-2H-isoindol-2-yl)]amine

Mix bis[3-(1,3-dihydro-1,3-dioxo-2H-isoindol-2-yl)]-t-butyloxycarbamide (4.43 g, 10 mmol) and 1N hydrochloric acid (50 mL) and stir under a nitrogen atmosphere at room temperature for 4 hours. Pour the reaction mixture into ethyl ether and separate the aqueous phase. Wash the aqueous phase with ethyl ether (2×), then neutralize with 5N sodium hydroxide. Extract into ethyl acetate, dry (MgSO₄) and evaporate the solvent in vacuo. Purify the residue by silica gel chromatography to give the title compound.

(Step c: Bis[3-(1,3-dihydro-1,3-dioxo-2H-isoindol-2-yl)])-ethanethiolamine 220

Dissolve bis[3-(1,3-dihydro-1,3-dioxo-2H-isoindol-2-yl)])amine (659 mg, 1.92 mmol) in anhydrous benzene (20 mL). Add, by dropwise addition, a solution of ethylene sulfide (116 mg, 1.92 mmol) in anhydrous benzene (10 mL) over several hours at reflux. Reflux for an additional 2 hours, filter throught Celite and evaporate the solvent in vacuo. Purify the residue by silica gel chromatography.

Step d: 5-Mercaptoethyl-1,5,9-triazanonane

Mix bis[3-(1,3-dihydro-1,3-dioxo-2H-isoindol-2-yl)])-ethanethiolamine (1.36 g, 3.38 mmol), hydrazine monohydrate (389 mg, 7.7 mmol) and methanol (38 mL) under a nitrogen atmosphere. Heat at reflux for 5 hours. Cool to ambient temperature and filter to remove phthaloyl hydrazide. Evaporate the filtrate in vacuo to a residue and slurry in chloroform (60 mL). Remove insoluble phthaloyl hydrazide by filtration and wash with chloroform (4×20 mL). Wash the filtrate with water (4×50 mL), dry (MgSO₄) and filter. Evaporate the filtrate in vacuo and purify the residue by silica gel chromatography to give the title compound.

Step e: 1,9-Bis[(phenyl)methyl]-5-ethanethiol-1,5,9-triazanonane

Dissolve 5-mercaptoethyl-1,5,9-triazanonane (955 mg, 0.005 mol) in methanol (distilled from Mg) (50 mL) and add benzadehyde (1.06 g, 0.01 mol), sodium cyanoborohydride (0.62 g, 0.010 mol) and 1 drop of 1% bromocresol green in ethanol. Maintain the pH of the reaction with 1N hydrochloric acid in methanol until the indicator no longer changes. Evaporate the solvent in vacuo and partition the residue between 1N sodium hydroxide (50 mL) and ethyl acetate (100 mL). Separate the organic phase, dry (MgSO₄) and evaporate the solvent in vacuo and purify by silica gel chromatography to give the title compound.

The following compounds can be prepared analogously to that described in Example 7:

1,9-Bis[(phenyl)methyl]-5-ethylphosphorothioate-1,5,9-triazanonane;

1,11-Bis[(phenyl)ethyl]-6-ethanethiol-1,6,11-triazaundecane.

The compounds of formula (2) wherein $B_1$ is —(CH₂)$_q$—SH or —(CH₂)$_q$—SPO₃H₂, $B_2$ and A are both hydrogen and n=1, 2 or 3 can be prepared according to the general synthetic scheme set forth in Scheme H wherein all substituents, unless otherwise indicated, are previously defined.

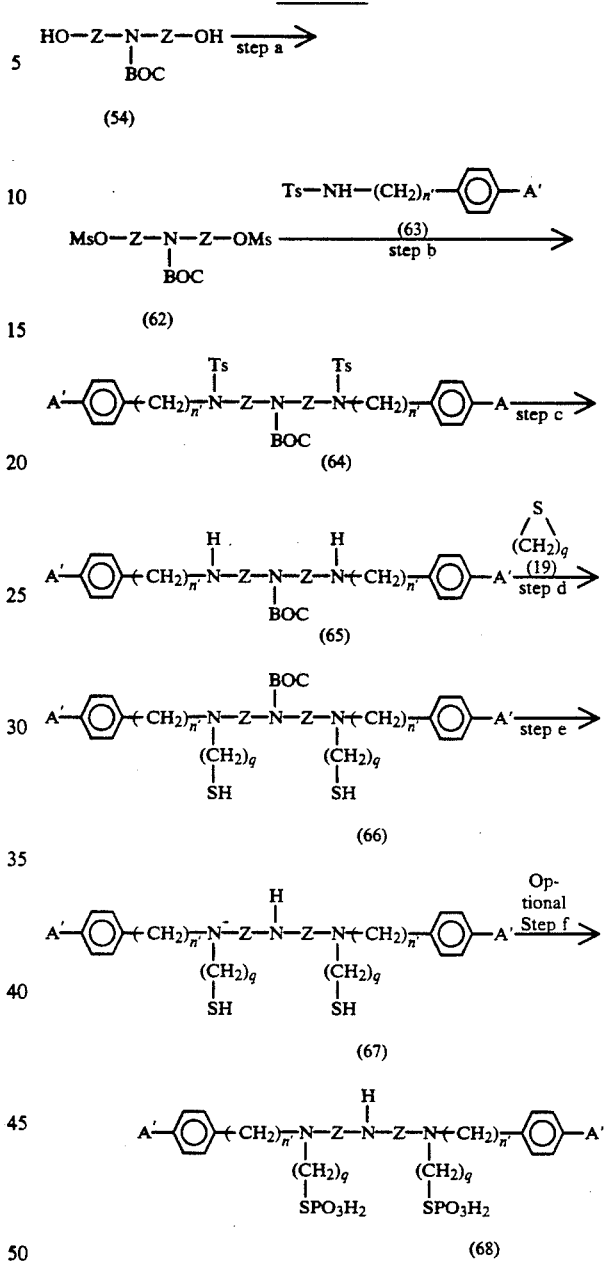

Scheme H $A' = —H$,
$n' = 1, 2$ or $3$

In step a, the appropriate bis(hydroxyalkyl)-t-butyloxycarbamide of structure (54) is converted to the corresponding bis[3-(methanesulfonylate)alkyl]-t-butyloxycarbamide of structure (62).

For example, the appropriate bis(hydroxyalkyl)-t-butyloxycarbamide of structure (54) is contacted with 2 molar equivalents of methanesulfonyl chloride. The reactants are typically contacted in an organic base, such as pyridine. The reactants are typically stirred together for a period of time ranging from 2–24 hours and at a temperature range of from 0° C. to room temperature. The bis[3-(methanesulfonylate)alkyl]-t-butyloxycarbamide of structure (62) is recovered from the reaction zone by extractive methods as is known in the art.

In step b, the bis[3-(methanesulfonylate)alkyl]functionalities of the appropriate bis[3-(methanesulfonylate)alkyl]-t-butyloxycarbamide of structure (62) are displaced with an appropriate (phenyl)alkyl-(4-methylphenyl)sulfonamide of structure (63) to give the corresponding bis[(phenyl)alkyl]-bis[(4-methylphenyl)sulfonyl]-(t-butyloxycarbonyl)-triazaalkane of structure (64) as described previously in Scheme B, step b.

In step c, the bis[(4-methylphenyl)sulfonyl]functionalities of the appropriate bis[(phenyl)alkyl]-bis[(4-methylphenyl)sulfonyl]-(t-butyloxycarbonyl)-triazaalkane of structure (64) are removed to give the corresponding bis[(phenyl)alkyl]-(t-butyloxycarbonyl)-triazaalkane of structure (65) as described previously in Scheme B, step e.

In step d, the bis[(phenyl)alkyl]amine functionalities of the appropriate bis[(phenyl)alkyl]-(t-butyloxycarbonyl)-triazaalkane of structure (65) are alkylated with an appropriate thioalkylating agent of structure (19) to give the appropriate bis[(phenyl)alkyl]-bis(alkylthiol)-(t-butyloxycarbonyl)-triaazaalkane of structure (66) as described previously in Scheme B, step f.

In step e, the t-butyloxycarbonyl functionality of the appropriate bis[(phenyl)alkyl]-bis(alkylthiol)-(t-butyloxycarbonyl)-triaazaalkane of structure (66) is removed to give the corresponding bis[(phenyl)alkyl]-bis(alkylthiol)-triazaalkane of structure (67) as described previously in Scheme B, step c.

In optional step f, the thiol functionality or functionalities of the appropriate compounds of formula (2) wherein A and $B_2$ are both hydrogen, $B_1$ is represented by $-(CH_2)_q-SH$ and n=1, 2 or 3 (structure 67) may be converted to the corresponding phosphorothioates to give those compounds of formula (2) wherein A and $B_2$ are both hydrogen, $B_1$ is represented by $-(CH_2)_q-SPO_3H_2$ and n=1, 2 or 3 (structure 68) as described previously in Scheme A, optional step f.

Starting materials for use in Scheme H are readily availiable to one of ordinary skill in the art. For example, (phenyl)methyl-(4-methylphenyl)sulfonamide is described in *J. Am. Chem. Soc.*, 85, 1152 1964.

The following example presents a typical synthesis as described in Scheme H. This example is understood to be illustrative only and is not intended to limit the scope of the present invention in any way.

EXAMPLE 8

1,9-Bis[(phenyl)methyl]-1,9-bis(ethanethiol)-1,5,9-triazanonane

Step a:

Bis[3-(methanesulfonylate)propyl]-t-butyloxycarbamide

Dissolve bis(3-hydroxypropyl)-t-butyloxycarbamide (2.33 g, 10 mmol) in anhydrous pyridine (25 mL) and cool to 5° C. Add, by dropwise addition, methanesulfonyl chloride (2.53 g, 22 mmol) and stir overnight. Partition between water and ethyl acetate and separate the organic phase. Wash the organic phase with cold 1N hydrochloric acid, saturated sodium hydrogen carbonate and brine. Dry (MgSO₄) and evaporate the solvent in vacuo to give the title compound.

Step b:

1,9-Bis[(phenyl)methyl]-1,9-bis[(4-methylphenyl)sulfonyl]-5-(t-butyloxycarbonyl)-1,5,9-triazanonane Suspend sodium hydride (4.8 g, 0.2 mol) in anhydrous dimethylformamide (100 mL), cool to 0° C. and place under a nitrogen atmosphere. Add, by dropwise addition, a solution of (phenyl)methyl-(4-methylphenyl)sulfonamide (26.1 g, 0.1 mol) in dimethylformamide. Stir until evolution of hydrogen ceases. Add, by dropwise addition, a solution of bis[3-(methanesulfonylate)propyl]-t-butyloxycarbamide (78 g, 0.2 mol) in dimethylformamide (200 mL). Stir overnight at room temperature then carefully quench with saturated ammonium chloride. Extract into ethyl acetate, dry (MgSO₄) and evaporate the solvent in vacuo. Purify by silica gel chromatogaphy to give the title compound.

Step c:

1,9-Bis[(phenyl)methyl]-5-(t-butyloxycarbonyl)-1,5,9-triazanonane

Mix 1,9-bis[(phenyl)methyl]-1,9-bis[(4-methylphenyl)sulfonyl]-5-(t-butyloxycarbonyl)-1,5,9-triazanonane (720 mg, 1 mmol) in dry liquid ammonia (25 mL) at −40° C. Add small pieces of sodium until a permanent blue color remains. Discharge the excess sodium with saturated ammonium chloride. Allow the ammonia to evaporate spontaneously and partition the residue between ethyl acetate and water. Separate the organic phase, dry (MgSO₄) and evaporate the solvent in vacuo. Purify by silica gel chromatography to give the title compound.

Step d:

1,9-Bis[(phenyl)methyl]-1,9-bis(ethanethiol)-5-(t-butyloxycarbonyl)-1,5,9-triazanonane Dissolve 1,9-bis[(phenyl)methyl]-5-(t-butyloxycarbonyl)-1,5,9-triazanonane (789 mg, 1.92 mmol) in anhydrous benzene (20 mL). Add, by dropwise addition, a solution of ethylene sulfide (232 mg, 3.84 mmol) in anhydrous benzene (10 mL) over several hours at reflux. Reflux for an additional 2 hours, filter throught Celite and evaporate the solvent in vacuo. Purify the residue by silica gel chromatography.

Step e:

1,9-Bis[(phenyl)methyl]-1,9-bis(ethanethiol)-1,5,9-triazanonane

Dissolve 1,9-bis[(phenyl)methyl]-1,9-bis(ethanethiol)-5-(t-butyloxycarbonyl)-1,5,9-triazanonane (531 mg, 1 mmol) in saturated methanolic hydrochloric acid. Stir for several hours and evaporate the solvent in vacuo. Dissolve the residue in water and neutralize with saturated sodium hydrogen carbonate and extract with ethyl acetate. Dry (MgSO₄) and evaporate the solvent in vacuo. Purify by silica gel chromatography to give the title compound.

The following compounds can be prepared analogously to that described in Example 8:

1,9-Bis[(phenyl)methyl]-1,9-bis(propanethiol)-1,5,9-triazanonane;

1,11-Bis[(phenyl)ethyl]-1,11-bis(ethanethiol)-1,6,11-triazaundecane;

1,9-Bis[(phenyl)ethyl]-1,9-bis(ethanethiol)-1,5,9-triazanonane.

The compounds of formula (2) wherein $B_1$ and $B_2$ are hydrogen, A is other than hydrogen and n=1, 2 or 3 can be prepared according to the general synthetic scheme set forth in Scheme I wherein all substituents, unless otherwise indicated, are previously defined.

Scheme I

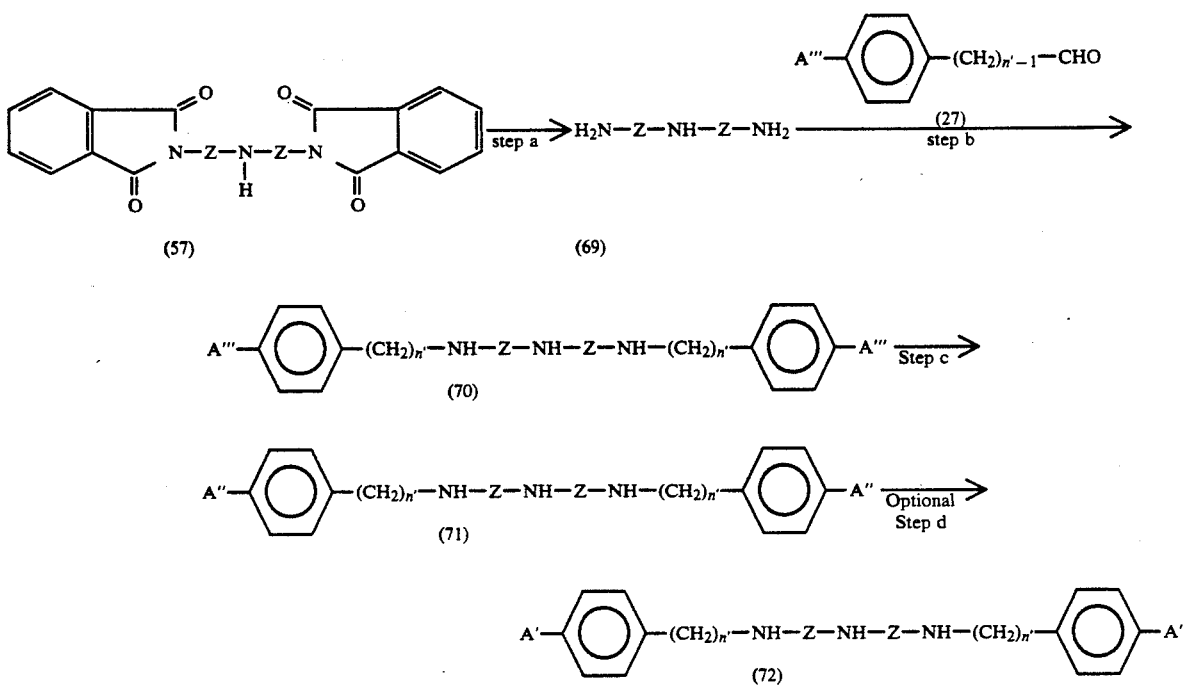

A''' = —SPg, —N(CH2)q—SPg
A'' = —SH, —N—(CH2)q—SH
A' = —SPO3H2, —N—(CH2)q—SPO3H2
n' = 1, 2 or 3

In step a, the phthalimide functionalities of the appropriate bis[3-(1,3-dihydro-1,3, dioxo-2H-isoindol-2-yl)][-amine of structure (57) are removed to give the corresponding triazaalkane of structure (69) as described previously in Scheme G, step d.

In step b, the terminal amino functionalities of the appropriate triazaalkane of structure (69) are reductively aminated with the appropriate thiol-protected (phenylthiol)-alkylaldehyde of structure (27) to give the appropriate thiol-protected bis[(phenyl)alkyl]-triazaalkane of structure (70) as described previously in Scheme A, step d.

In step c, the protecting groups on the thiol functionalities of the appropriate thiol-protected bis[(phenyl)alkyl]-triazaalkane of structure (70) are removed to give the corresponding bis[(phenyl)alkyl]-triazaalkane of structure (71) by techniques and procedures well known and appreciated by one of ordinary skill in the art and as described previously in Scheme C, step e.

In optional step d, the thiol functionalities of the appropriate compounds of formula (2) wherein A is a group represented by —SH or —N—(CH2)q—SH, B1 and B2 are both hydrogen and n=1, 2 or 3 (structure 71) may be converted to the corresponding phosphorothioates to give those compounds of formula (2) wherein A is a group represented by —SPO3H2 or —N—(CH2.)q—SPO3H2, B1 and B2 are both represented by hydrogen and n=1, 2 or 3 (structure 72) as described previously in Scheme A, optional step f.

Starting materials for use in Scheme I are readily availiable to one of ordinary skill in the art.

The following example presents a typical synthesis as described in Scheme I.

EXAMPLE 9

1,9-Bis[(4-mercaptophenyl)methyl]-1,5,9-triazanonane, trihydrohloride

Step a: 1,5,9-triazanonane

Mix bis[3-(1,3-dihydro-1,3-dioxo-2H-isoindol-2-yl)]amine (1.24 g, 3.38 mmol), hydrazine monohydrate (389 mg, 7.7 mmol) and methanol (38 mL) under a nitrogen atmosphere. Heat at reflux for 5 hours. Cool to ambient temperature and filter to remove phthaloyl hydrazide. Evaporate the filtrate in vacuo to a residue and slurry in chloroform (60 mL). Remove insoluble phthaloyl hydrazide by filtration and wash with chloroform (4×20 mL). Wash the filtrate with water (4×50 mL), dry (MgSO4) and filter. Evaporate the filtrate in vacuo and purify the residue by silica gel chromatography to give the title compound.

Step b:
1,9-Bis[(4-methylmercaptophenyl)methyl]-1,5,9-triazanonane

Dissolve 1,5,9-triazanonane (655 mg, 0.005 mol) in methanol (distilled from Mg) (50 mL) and add 4-(methylthio)benzaldehyde (1.52 g, 0.01 mol), sodium cyanoborohydride (0.62 g, 0.010 mol) and 1 drop of 1% bromocresol green in ethanol. Maintain the pH of the reaction with 1N hydrochloric acid in methanol until the indicator no longer changes. Evaporate the solvent in vacuo and partition the residue between 1N sodium hydroxide (50 mL) and ethyl acetate (100 mL). Separate the organic phase, dry (MgSO4) and evaporate the solvent in vacuo and purify by silica gel chromatography to give the title compound.

Step c:
1,9-Bis[(4-mercaptophenyl)methyl]-1,5,9-triazanonane, trihydrochloride Dissolve 1,9-bis[(4-methylmercaptophenyl)methyl]-1,5,9-triazanonane (2.02 g, 5 mmol) in chloroform (20 mL) and treat with metachloroperbenzoic acid (863 mg, 5 mmol). Add calcium hydroxide (556 mg, 7.5 mmol) and stir for 15 minutes. Filter and evaporate the solvent in vacuo. Dissolve the residue in trifluoroacetic anhydride (10 mL) and heat at reflux for 30 minutes. Evaporate the volatiles in vacuo and dissolve the residue in a mixture of methanol-triethylamine (1:1, 100 mL) and evaporate the solvent in vacuo. Dissolve the resdiue in chloroform, wash with saturated ammonium chloride and dry (MgSO$_4$). Evaporate the solvent in vacuo to give the crude 1,9-bis[(4-mercaptophenyl)methyl]-1,5,9-triazanonane.

Dissolve the crude 1,9-bis[(4-mercaptophenyl)methyl]-1,5,9-triazanonane (1.88 g, 5 mmol) in 50/50 dioxane/water (25 mL) and buffer to pH 10 with 1N sodium hydroxide. Add, by dropwise addition, an ether solution of di-t-butyl dicarbonate (4.8 g, 22 mmol) at 10° C. Allow to warm to room temperature and buffer occasionally to retain pH 10. Acidify with a sodium citrate/citric acid buffer to pH 5, extract with ether (3×), dry (MgSO$_4$) and evaporate the solvent in vacuo. Purify the residue by silica gel chromatography to give 1,9-bis[(4-mercaptophenyl)methyl]-1,5,9-tri(t-butyloxycarbonyl)-1,5,9-triazanonane.

Dissolve 1,9-bis[(4-mercaptophenyl)methyl]-1,5,9-tri(t-butyloxycarbonyl)-1,5,9-triazanonane (4.75 g, 10 mmol) in saturated methanolic hydrochloric acid (100 mL). Stir for several hours and evaporate the solvent in vacuo to give the title compound.

The following compound can be prepared analogously to that described in Example 9:

1,11-Bis[(4-mercaptophenyl)ethyl]-1,6,11-triazaundecane, trihydrochloride;
1,9-Bis[(4-(2-thioethylanilinyl)methyl]-1,5,9-triazanonadecane, trihydrochloride;
1,9-Bis[(4-(2-ethylphosphorothioateanilinyl)methyl]-1,5,9-triazanonadecane, trihydrochloride The compounds of formula (2) wherein A and B$_1$ are both hydrogen, B$_2$ is a group represented by —(CH$_2$)$_q$SH or —(CH$_2$)$_q$SPO$_3$H$_2$ and n=0 can be prepared according to the general synthetic scheme set forth in Scheme J wherein all substituents, unless otherwise indicated, are previously defined.

Scheme J

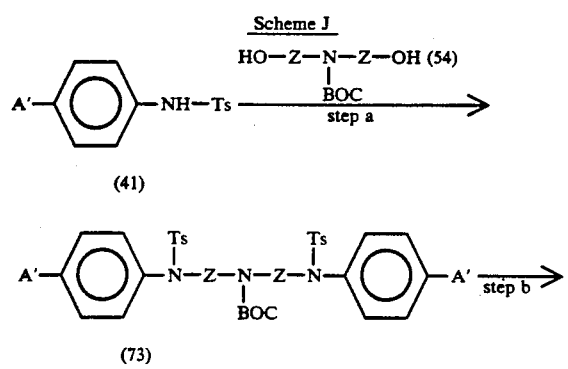

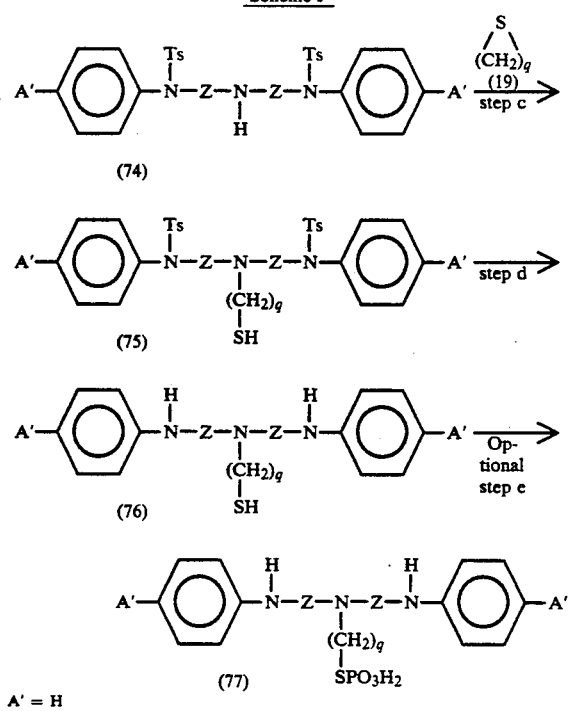

A' = H

In step a, the appropriate N-[(4-methylphenyl)sulfonyl]-aniline of structure (41) is alkylated with an appropriate bis (hydroxyalkyl)-t-butyloxycarbamide of structure (54) to give the appropriate bis[phenyl]-bis[(4-methylphenyl)sulfonyl]-(t-butyloxycarbonyl)-triazaalkane of structure (73).

For example, the appropriate N-[(4-methylphenyl)sulfonyl]aniline of structure (41) is contacted with a molar excess of triphenylphosphine, a molar deficiency of the appropriate bis(hydroxyalkyl)-t-butyloxycarbamide of structure (54) and a molar excess of diethyl azodicarboxylate. The reactants are typically contacted in a suitable organic solvent such as tetrahydrofuran. The reactants are typically stirred together at room temperature for a period of time ranging from 2-24 hours. The bis[phenyl]-bis[(4-methylphenyl)sulfonyl]-(t-butyloxycarbonyl)-triazaalkane of structure (73) is recovered from the reaction zone by evaporation of the solvent. It can be purified by silica gel chromatography.

In step b, the tert-butyloxycarbonyl functionality of the appropriate bis[phenyl]-bis[(4-methylphenyl)sulfonyl]-(t-butyloxycarbonyl)-triazaalkane of structure (73) is hydrolyzed to give the appropriate bis[phenyl]-bis[(4-methylphenyl)sulfonyl]-triazaalkane of structure (74) as described previously in Scheme Scheme B, step c.

In step c, the amine functionality of the appropriate bis[phenyl]-bis[(4-methylphenyl)sulfonyl]-triazaalkane of structure (74) is alkylated with an appropriate thioalkylating agent of structure (19) to give the appropriate bis[phenyl]-bis(alkylthiol)-bis[(4-methylphenyl)sulfonyl]-triazaalkane of structure (75) as described previously in Scheme B, step f.

In step d, the sulfonamide functionalities of the appropriate bis[phenyl]-bis(alkylthiol)-bis[(4-methylphenyl)sulfonyl]-triazaalkane of structure (75) are cleaved to give the appropriate bis[phenyl]-(alkylthiol)triazaalkane of structure (76) as described previously in Scheme B, step e.

In optional step e, the thiol functionality of the appropriate compounds of formula (2) wherein $B_2$ is a group represented by -$(CH_2)_9$—SH, A and $B_1$ are both hydrogen and n=0 (structure 76) may be converted to the corresponding phosphorothioate to give those compounds of formula (2) wherein $B_2$ is a group represented by —$(CH_2)_q$—$SPO_3H_2$, A and $B_1$ are both represented by hydrogen and n=0 (structure 77) as described previously in Scheme A, optional step f.

Starting materials for use in Scheme J are readily available to one of ordinary skill in the art.

The following example presents a typical synthesis as described in Scheme J. This example is illustrative only and is not intended to limit the scope of the present invention in any way.

EXAMPLE 10

1,9-Bis[phenyl]-5-(ethanethiol)-1, 5,9-triazanonane, trihydrochloride

Step a:
1,9-Bis[phenyl]-1,9-bis[(4-methylphenyl)sulfonyl]-5-(t-butyloxycarbonyl)-1,5,9-triazanonane Dissolve bis(3-hydroxypropyl)amine (1.33 g, 10 mmol) in 50/50 dioxane/water (25 mL) and buffer to pH 10 with 1N sodium hydroxide. Add, by dropwise addition, an ether solution of t-butyl azidoformate (1.58 g, 11 mmol) at 10° C. Allow to warm to room temperature and buffer occasionally to retain pH 10.

Acidify with a sodium citrate/citric acid buffer to pH 5, extract with ether (3×), dry (MgSO₄) and evaporate the solvent in vacuo. Purify the residue by silica gel chromatography to give bis(3-hydroxypropyl)-t-butyloxycarbamide.

Dissolve N-[(4-methylphenyl)sulfonyl]aniline (106 mg, 0.43 mmol) in anhydrous tetrahydrofuran (3 mL) and add triphenylphosphine (168 mg, 0.645 mmol). Stir under a nitrogen atmosphere and add bis(3-hydroxypropyl)-t-butyloxycarbamide (83.6 mg, 0.215 mmol) followed by diethyl azodicarboxylate (0.083 mL, 0.530 mmol). Stir at room temperature for several hours and evaporate the solvent in vacuo. Purify by silica gel chromatography to give the title compound.

Step b:
1,9-Bis[phenyl]-1,9-bis[(4-methylphenyl)sulfonyl]-1,5,9-triazanonane

Dissolve 1,9-bis[(phenyl)]-1,9-bis[(4-methylphenyl)-sulfonyl]-5-(t-butyloxycarbonyl)-1,5,9-triazanonane (691 mg, 1 mmol) in saturated methanolic hydrochloric acid (10 mL). Stir for several hours and evaporate the solvent in vacuo. Dissolve the residue in water and neutralize with saturated sodium hydrogen carbonate and extract with ethyl acetate. Dry (MgSO₄) and evaporate the solvent in vacuo. Purify by silica gel chromatography to give the title compound.

Step c:
1,9-Bis[phenyl]-1,9-bis[(4-methylphenyl)sulfonyl]-5-(ethanethiol)-1,5,9-triazanonane Dissolve 1,9-bis[phenyl]-1,9-bis[(4-methylphenyl)sulfonyl]-1,5,9-triazanonane (1.13 g 1.92 mmol) in anhydrous benzene (20 mL). Add, by dropwise addition, a solution of ethylene sulfide (242 mg 9, 4 mmol) in anhydrous benzene (10 mL) over several hours at reflux. Reflux for an additional 2 hours, filter throught Celite and evaporate the solvent in vacuo. Purify the residue by silica gel chromatography.

Step f:
1,9-Bis[phenyl]-5-(ethanethiol)-1,5,9-triazanonane

Mix 1,9-bis[phenyl]-1,9-bis[(4-methylphenyl)sulfonyl]-5-(ethanethiol)-1,5,9-triazanonane (651 mg, 1 mmol) in dry liquid ammonium (25 mL) at −40° C. Add small pieces of sodium until a permanent blue color remains. Discharge the excess sodium with saturated ammonium chloride. Allow the ammonium to evaporate spontaneously and partition the residue between ethyl acetate and water. Separate the organic phase, dry (MgSO₄) and evaporate the solvent in vacuo. Purify by silica gel chromatography to give the title compound.

The following compounds may be prepared analogously to that described in Example 10:
1,11-Bis[phenyl]-6-(propanethiol)-1,6,11-triazaundecane;
1,9-Bis[phenyl]-5-(ethylphosphorothioate)-1,5,9-triazanonadecane.

The compounds of formula (2) wherein A and $B_2$ are both hydrogen, $B_1$ is a group represented by —$(CH_2)_q$SH or —$(CH_2)_q$SPO₃H₂ and n=0 can be prepared according to the general synthetic scheme set forth in Scheme K wherein all substituents, unless otherwise indicated, are previously defined.

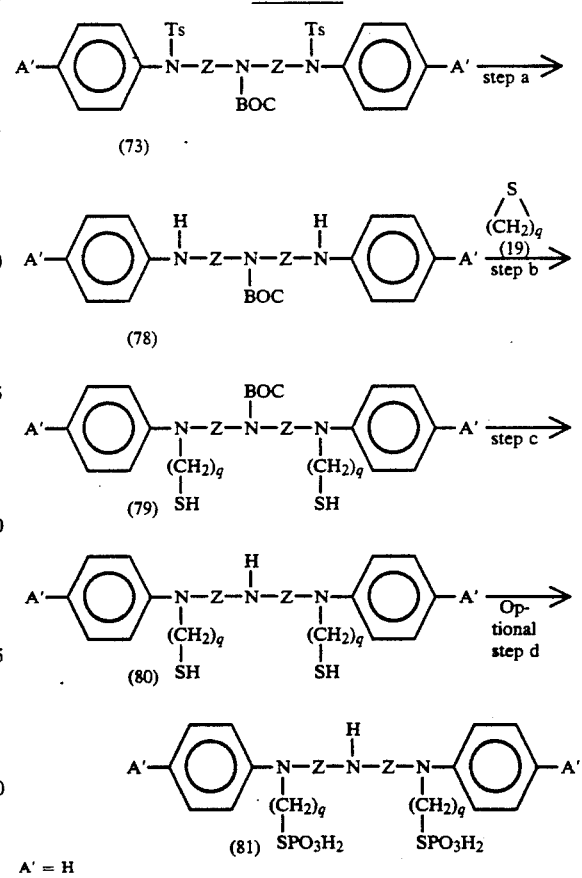

A' = H

In step a, the sulfonamide functionalities of the appropriate bis[phenyl]-bis[(4-methylphenyl)sulfonyl]-(t-butyloxycarbonyl)-triazaalkane of structure (73) are cleaved to give the appropriate bis[phenyl]-(t-butyloxycarbonyl)triazaalkane of structure (78) as described previously in Scheme B, step e.

In step b, the amine functionalities of the appropriate bis[phenyl]-(t-butyloxycarbonyl)-triazaalkane of structure (78) are alkylated with an appropriate thioalkylating agent of structure (19) to give the appropriate bis[phenyl]bis(alkylthiol)-(t-butyloxycarbonyl)-triazaalkane of structure (79) as described previously in Scheme B, step f.

In step c, the tert-butyloxycarbonyl functionality of the appropriate bis[phenyl]-bis(alkylthiol)-(t-butyloxycarbonyl)-triazaalkane of structure (79) is hydrolyzed to give the appropriate bis[phenyl]bis(alkylthiol)-triazaalkane of structure (80) as described previously in Scheme B, step c.

In optional step d, the thiol functionalities of the appropriate compounds of formula (2) wherein $B_1$ is a group represented by —$(CH_2)_q$—SH, A and $B_2$ are both hydrogen and n=0 (structure 80) may be converted to the corresponding phosphorothioates to give those compounds of formula (2) wherein $B_1$ is a group represented by —$(CH_2)_q$—$SPO_3H_2$, A and $B_2$ are both represented by hydrogen and n=0 (structure 81) as described previously in Scheme A, optional step f.

Starting materials for use in Scheme K are readily available to one of ordinary skill in the art.

The following example presents a typical synthesis as described in Scheme K. This example is illustrative only and is not intended to limit the scope of the present invention in any way.

EXAMPLE 11

1,9-Bis[phenyl]-1,9-bis(mercaptoethyl)-1,5,9-triazanonane, trihydrochloride

Step a:
1,9-Bis[phenyl]-5-(t-butyloxycarbonyl)-1,5,9-triazanonane

Mix 1,9-bis[(phenyl)]-1,9-bis[(4-methylphenyl)sulfonyl]-5-(t-butyloxycarbonyl)-1,5,9-triazanonane (691 mg, 1 mmol) in dry liquid ammonia (25 mL) at −40° C. Add small pieces of sodium until a permanent blue color remains. Discharge the excess sodium with saturated ammonium chloride. Allow the ammonia to evaporate spontaneously and partition the residue between ethyl acetate and water. Separate the organic phase, dry (MgSO₄) and evaporate the solvent in vacuo. Purify by silica gel chromatography to give the title compound.

Step b:
1,9-Bis[phenyl]-1,9-bis(mercaptoethyl-5-(t-butyloxycarbonyl)-1,5,9-triazanonane Dissolve 1,9-bis[phenyl]-5-(t-butyloxycarbonyl)-1,5,9-triazanonane (735 mg, 1.92 mmol) in anhydrous benzene (20 mL). Add, by dropwise addition, a solution of ethylene sulfide (242 mg, 4 mmol) in anhydrous benzene (10 mL) over several hours at reflux. Reflux for an additional 2 hours, filter through Celite and evaporate the solvent in vacuo. Purify the residue by silica gel chromatography.

Step c:
1,9-Bis[phenyl]-1,9-bis(mercaptoethyl)-1,5,9-triazanonane, trihydrochloride Dissolve 1,9-bis[phenyl]-1,9-bis(mercaptoethyl-5-(t-butyloxycarbonyl)-1,5,9-triazanonane (711 mg, 1 mmol) in saturated methanolic hydrochloric acid. Stir for several hours and evaporate the solvent in vacuo to give the title compound.

The following compounds may be prepared analogously to that described in Example 11:

1,11-Bis[phenyl]-1,11-bis(mercaptopropyl)-1,6,11-triazaundecane, trihydrochloride;

1,9-Bis[phenyl]-1,9-bis(ethylphosphorothioate)-1,5,9-triazanonadecane, trihydrochloride.

The compounds of formula (2) wherein $B_1$ and $B_2$ are both hydrogen, A is other then hydrogen and n=0 can be prepared according to the general synthetic scheme set forth in Scheme L wherein all substituents, unless otherwise indicated, are previously defined.

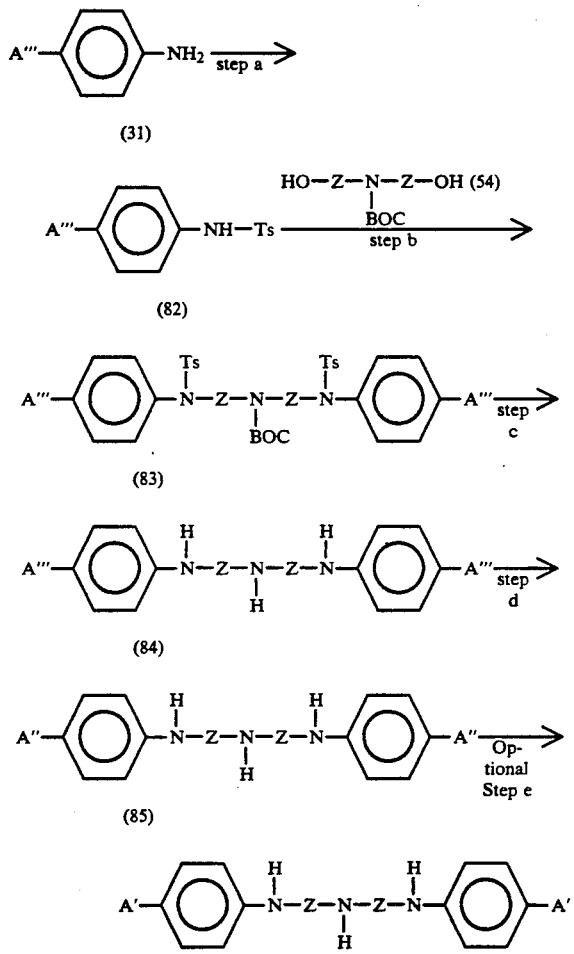

In step a, the appropriate thiol-protected (mercapto)aniline of structure (31) is converted to the corresponding thiol-protected N-[(4-methylphenyl)sulfonyl]-(mercaptophenyl)amine of structure (82) as described previously in Scheme E, step a.

In step b, the the appropriate thiol-protected N-[(4-methylphenyl)sulfonyl]-(mercaptophenyl)amine of structure (82) is alkylated with an appropriate bis(hydroxyalkyl)-t-butyloxycarbamide of structure (54) to give the appropriate thiol-protected bis[mercaptophenyl]-bis[(4-methylphenyl)sulfonyl]-(t-butyloxycarbonyl)-triazaalkane of structure (83) as described previously in Scheme J, step a.

In step c, the N-protecting groups of the appropriate thiol-protected bis[mercaptophenyl]-bis[(4-methylphenyl)sulfonyl]-(t-butyloxycarbonyl)-triazaalkane of structure (83) are hydrolyzed to give the corresponding thiol-protected bis[mercaptophenyl]-triazaalkane of structure (84).

For example, the appropriate thiol-protected bis[mercaptophenyl]-bis[(4-methylphenyl)sulfonyl]-(t-butyloxycarbonyl)-triazaalkane of structure (83) is contacted with a molar excess of an appropriate acid, such as hydrobromic acid. The reactants are typically contacted for a period of time ranging from 2–24 hours and at a temperature range of from room temperature to reflux. The thiol-protected bis[mercaptophenyl]-triazaalkane of structure (84) is recovered from the reaction zone by extractive methods as is known in the art. It can be purified by silica gel chromatography.

In step d, the the thiol-protecting groups of the appropriate thiol-protected bis[mercaptophenyl]-triazaalkane of structure (84) are removed to give the corresponding bis[mercaptophenyl]-triazaalkane of structure (85) using techniques and procedures well known and appreciated by one of ordinary skill in the art.

In optional step e, the thiol functionalities of the appropriate compounds of formula (2) wherein A is a group represented by —SH or —N—$(CH_2)_q$—SH, $B_1$ and $B_2$ are both hydrogen and n=0 (structure 85) may be converted to the corresponding phosphorothioates to give those compounds of formula (2) wherein A is a group represented by —$SPO_3H_2$ or —N—$(CH_2)_q$—S-$PO_3H_2$, $B_1$ and $B_2$ are both represented by hydrogen and n=0 (structure 86) as described previously in Scheme A, optional step f.

Starting materials for use in Scheme L are readily available to one of ordinary skill in the art.

The following example presents a typical synthesis as described in Scheme L. This example is illustrative only and is not intended to limit the scope of the present invention in any way.

EXAMPLE 12

Bis(4-mercaptophenyl)-1,5,9-triazanonane

Step a:
N-[(4-Methylphenyl)sulfonyl]-(4-methylmercaptophenyl)amine

Dissolve 4-(methylmercapto) aniline (1.39 g, 10 mmol) in anhydrous pyridine (25 mL) and cool to 5° C. Add, by dropwise addition, p-toluenesulfonyl chloride (2.1 g, 11 mmol) and stir overnight. Partition between water and ethyl acetate and separate the organic phase. Wash the organic phase with cold 1N hydrochloric acid, saturated sodium hydrogen carbonate and brine. Dry ($MgSO_4$) and evaporate the solvent in vacuo to give the title compound.

Step b:
1,9-Bis(4-methylmercaptophenyl)-1,9-bis[(4-methylphenyl)sulfonyl]-5-(t-butyloxycarbonyl)-1,5,9-triazanonane Dissolve N-[(4-methylphenyl)sulfonyl]-(4-methylmercaptophenyl)amine (126 mg, 0.43 mmol) in anhydrous tetrahydrofuran (3 mL) and add triphenylphosphine (168 mg, 0.654 mmol). Stir under a nitrogen atmosphere and add bis(3-hydroxypropyl)-t-butyloxycarbamide (83.6 mg, 0.215 mmol) followed by diethylazodicarboxylate (0.083 mL, 0.530 mmol). Stir at room temperature for several hours and evaporate the solvent in vacuo. Purify be silica gel chromatography to give the title compound.

Step c:
1,9-Bis[4-methylmercaptophenyl]-1,5,9-triazanonane

Dissolve 1,9-bis(4-methylmercaptophenyl)-1,9-bis[(4-methylphenyl)sulfonyl]-5-(t-butyloxycarbonyl)-1,5,9-triazanonane (783 mg, 1 mmol) in 48% hydrobromic acid ( mL). Stir for several hours and evaporate the solvent in vacuo. Dissolve the residue in water and neutralize with saturated sodium hydrogen carbonate and extract with ethyl acetate. Dry ($MgSO_4$) and evaporate the solvent in vacuo. Purify by silica gel chromatography to give the title compound.

Step d: 1,9-Bis[4-mercaptophenyl]-1,5,9-triazanonane, trihydrochloride

Dissolve 1,9-bis[4-methylmercaptophenyl]-1,5,9-triazanonane (1.88 g, 5 mmol) in chloroform (20 mL) and treat with metachloroperbenzoic acid (863 mg, 5 mmol). Add calcium hydroxide (556 mg, 7.5 mmol) and stir for 15 minutes. Filter and evaporate the solvent in vacuo. Dissolve the residue in trifluoroacetic anhydride (10 mL) and heat at reflux for 30 minutes. Evaporate the volatiles in vacuo and dissolve the residue in a mixture of methanol-triethylamine (1:1, 100 mL) and evaporate the solvent in vacuo. Dissolve the resdiue in chloroform, wash with saturated ammonium chloride and dry ($MgSO_4$). Evaporate the solvent in vacuo to give the crude 1,9-bis[(4-mercaptophenyl))-1,5,9 triazanonane.

Dissolve the crude 1,9-bis[(4-mercaptophenyl)]-1,5,9-triazanonane (1.74 g, 5 mmol) in 50/50 dioxane/water (25 mL) and buffer to pH 10 with 1N sodium hydroxide. Add, by dropwise addition, an ether solution of di-t-butyl dicarbonate (4.8 g, 22 mmol) at 10° C. Allow to warm to room temperature and buffer occasionally to retain pH 10. Acidify with a sodium citrate/citric acid buffer to pH 5, extract with ether (3×), dry ($MgSO_4$) and evaporate the solvent in vacuo. Purify the residue by silica gel chromatography to give 1,9-bis[(4-mercaptophenyl)]-1,5,9-tri(t-butyloxycarbonyl)-1,5,9-triazanonane.

Dissolve 1,9-bis (4-mercaptophenyl)]-1,5,9-tri(t-butyloxycarbonyl)-1,5,9-triazanonane (6.48 g, 10 mmol) in saturated methanolic hydrochloric acid (100 mL). Stir for several hours and evaporate the solvent in vacuo to give the title compound.

The following compounds may be prepared analogously to that described in Example 12:
1,9-Bis[4-(2-thioethylanilinyl)]-1,5,9-triazanonane, trihydrochloride;
1,11-Bis[4-(2-ethylphosphorothioateanilinyl)]-1,6,11-triazaundecane, trihydrochloride
1,11-Bis[(4-mercaptophenyl)]-1,6,11-triazaundecane, trihydrochloride.

The present invention provides a method of protecting cells from deleterious cellular effects caused by exposure to ionizing radiation or by exposure to a DNA-reactive agent.

Ionizing radiation is high energy radiation, such as an X-ray or a gamma ray, which interacts to produce ion pairs in matter. Exposure to ionizing radiation may occur as the result of environmental radiation, such as resulting from a nuclear explosion, a spill of radioactive material, close proximity to radioactive material and the like. More commonly, exposure to ionizing radiation may occur as the result of radiological medical procedures such as radiation therapy for various types of cancers.

DNA-reactive agents are those agents, such as alkylating agents, cross-linking agents, and DNA intercalating agents, which interact covalently or non-covalently with cellular DNA causing certain deleterious cellular effects. For example, DNA-reactive agents include cisplatin, cyclophosphamide, diethylnitrosoamine, benzo(a)pyrene, carboplatin, doxorubicin, mitomycin-C and the like. Many of these DNA-reactive agents, such as cisplatin, cyclophosphamide, doxorubicin and mitomycin-C are useful in cancer therapy as DNA-reactive chemotherapeutic agents.

Deleterious cellular effects caused by exposure to ionizing radiation or to a DNA-reactive agent include damage to cellular DNA, such as DNA strand break, disruption in cellular function, such as by disrupting DNA function, cell death, tumor induction, such as therapy-induced secondary tumor induction, and the like. These deleterious cellular effects can lead to secondary tumors, bone marrow suppression, kidney damage, peripheral nerve damage, gastro-intestinal damage and the like. For example, in cancer radiation therapy, the exposure to radiation is intended to cause cell death in the cancer cells. Unfortunately, a large part of the adverse events associated with the therapy is caused by these deleterious cellular effects of the radiation on normal cells as opposed to cancer cells.

The present invention provides a method by which cells are protected from deleterious cellular effects by preventing or eliminating these effects or by reducing their severity. According to the present invention, the cells to be protected are contacted with a compound of formula (1) or (2) prior to or during exposure of the cell to ionizing radiation or to DNA-reactive agents. The cells may be contacted directly, such as by applying a solution of a compound of the invention to the cell or by administering a compound of the invention to a mammal. The compounds of the present invention thus provide a protective effect in the cell which eliminates or reduces the severity of the deleterious cellular effects which would otherwise be caused by the exposure.

More particularly, the present invention provides a method of protecting non-cancer, or normal, cells of a mammal from deleterious cellular effects caused by exposure of the mammal to ionizing radiation or to a DNA-reactive agent. As used herein, the term "mammal" refers to warm-blooded animals such as mice, rats, dogs and humans. The compounds of the present invention provide a selective protection of normal cells, and not of cancer cells, during cancer radiation therapy and during chemotherapy with a DNA-reactive chemotherapeutic agent. According to the present invention the compound of the invention is administered to the mammal prior to or during exposure to ionizing radiation or to a DNA-reactive agent. The present invention provides a method whereby the deleterious cellular effects on non-cancer cells caused by exposure of the mammal to ionizing radiation or to a DNA-reactive agent are eliminated or reduced in severity or in extent.

In addition, the present invention provides a method of treating a patient in need of radiation therapy or in need of chemotherapy with a DNA-reactive chemotherapeutic agent. As used herein, the term "patient" refers to a mammal, including mice, rats, dogs and humans, which is afflicted with a neoplastic disease state or cancer such that it is in need of cancer radiation therapy or chemotherapy with a DNA-reactive chemotherapeutic agent. The term "neoplastic disease state" as used herein refers to an abnormal state or condition characterized by rapidly proliferating cell growth or neoplasm.

Neoplastic disease states for which treatment with a compound of formula (1) or (2) will be particularly useful in conjunction with radiation therapy or chemotherapy with a DNA-reactive chemotherapeutic agent include: Leukemias such as, but not limited to, acute lymphoblastic, acute myelogenous, chronic lymphocytic, acute myeloblastic and chronic myelocytic; Carcinomas, such as, but not limited to, those of the cervix, oesophagus, stomach, pancreas, breast, ovaries, small intestines, colon and lungs; Sarcomas, such as, but not limited to, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma, Hodgkin's disease and non-Hodgkin's lymphoma. Neoplastic disease states for which treatment with a compound of formula (1) or (2) will be particularly preferred in conjunction with radiation therapy or chemotherapy include Hodgkin's disease, pancreatic carcinoma, advanced carcinoma, breast cancers, ovarian cancer, colon cancers and the like.

In addition, treatment with a compound of the present invention provides selective protection against deleterious cellular effects, such as therapy-induced secondary tumor induction, caused by radiation therapy or chemotherapy with a DNA-reactive chemotherapeutic agent. Treatment with a compound of the present invention is thus useful in eliminating or reducing the risk of secondary tumor induction, such as therapy-induced acute myelogenous leukemia and non-Hodgkin's lymphoma, brought about by radiotherapy or chemotherapy for treatment of Hodgkin's disease.

According to the present invention, administration to a patient of a compound of formula (1) or (2) prior to or during radiation therapy or chemotherapy with a DNA-reactive chemotherapeutic agent will provide a selective protection of non-cancer cells of the patient but not of cancer cells. The deleterious cellular effects on non-cancer cells caused by treatment of the patient with ionizing radiation or with a DNA-reactive chemotherapeutic agent are thus eliminated or reduced in severity or in extent.

A protective amount of a compound of formula (1) or (2) refers to that amount which is effective, upon single or multiple dose administration to a mammal or patient, in eliminating or reducing in severity or in extent the deleterious cellular effects caused by exposure to or treatment with ionizing radiation or a DNA-reactive agent. A protective amount of a compound of formula (1) or (2) also refers to that amount which is effective, upon single or multiple dose administration to the cell, in eliminating or reducing in severity or in extent the deleterious cellular effects caused by exposure to ionizing radiation or a DNA-reactive agent.

A protective amount for administration to a mammal or a patient can be readily determined by the attending diagnostician, as one skilled in the art, by the use of known techniques and by observing results obtained under analogous circumstances. In determining the protective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

The compounds of formula (1) or (2) may be administered as single doses or as multiple doses and are ordinarily administered prior to and/or during exposure to ionizing radiation or to DNA-reactive agents. Generally, where a compound of the present invention is administered in conjunction with radiation therapy, the compound of the present invention will be administered in single or multiple doses prior to radiation therapy following a schedule calculated to provide the maximum selective protective effect during radiation therapy. Generally, where a compound of the present invention is administered in conjunction with a DNA-reactive chemotherapeutic agent, the compound of the present invention will be administered in single or multiple doses prior to and during chemotherapy following a schedule calculated to provide the maximum selective protective effect during chemotherapy.

The details of the dosing schedule for the compounds of the present invention necessary to provide the maximum selective protective effect upon exposure to ionizing radiation or to a DNA-reactive agent can be readily determined by an attending physician, as one skilled in the art, by the use of known techniques and by observing results obtained under analogous circumstances.

A protective amount of a compound of formula 1) or (2) for administration to a mammal or patient will vary from about 5 milligram per kilogram of body weight per day (mg/kg/day) to about 1000 mg/kg/day. Preferred amounts are expected to vary from about 50 to about 500 mg/kg/day.

A protective amount of a compound of formula (1) or (2) for contacting a cell will vary from about 100 micromolar to about 5 millimolar in concentration.

A compound of formula (1) or (2) can be administered to a mammal or a patient in any form or mode which makes the compound bioavailable in effective amounts, including oral and parenteral routes. For example, compounds of formula (1) and (2) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formula (1) or (2) in admixture or otherwise in association with one or more inert carriers. These compositions are useful, for example, as assay standards, as convenient means of making bulk shipments, or as pharmaceutical compositions. An assayable amount of a compound of formula (1) or (2) is an amount which is readily measurable by standard assay procedures and techniques as are well known and appreciated by those skilled in the art. Assayable amounts of a compound of formula (1) or (2) will generally vary from about 0.001% to about 75% of the composition by weight. Inert carriers can be any material which does not degrade or otherwise covalently react with a compound of formula (1) or (2). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula (1) or (2) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel TM, corn starch and the like; lubricants such as magnesium stearate or Sterotex TM; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula (1) or (2) in their end-use application.

Compounds of formula (1) wherein n is 1, m is 7 and Z is $-CH_2CH_2CH_2-$ are generally preferred. Compounds of formula (1) wherein A is H, $-SH$, $-NCH_2CH_2SH$ or $-NCH_2CH_2SPO_3H_2$ are generally preferred. Compounds of formula (1) wherein $B_1$ and $B_2$ are $CH_2CH_2SH$ or $-CH_2CH_2SPO_3H_2$ are preferred when A is H. Compounds of formula (1) wherein $B_1$ and $B_2$ are H are preferred when A is $-SH$, $-NCH_2CH_2SH$ or $-NCH_2CH_2SPO_3H_2$.

Compounds of formula (2) wherein n is 1 and Z is $-CH_2CH_2CH_2-$ are generally preferred. Compounds of formula (2) wherein A is H, $-SH$, $-NCH_2CH_2SH$ or $-NCH_2CH_2SPO_3H_2$ are generally preferred. Compounds of formula (2) wherein $B_1$ and $B_2$ are $CH_2CH_2SH$ or $-CH_2CH_2SPO_3H_2$ are preferred when A is H. Compounds of formula (2) wherein $B_1$ and $B_2$ are H are preferred when A is $-SH$, $-NCH_2CH_2SH$ or $-NCH_2CH_2SPO_3H_2$.

The utility of the compounds of the present invention may be demonstrated as radioprotective agents both in vitro and in vivo.

For example, the ability of cultured cells to form clones (colonies) may be evaluated as a function of exposure to X-ray dose or chemical dose. Cells are either not drug treated or are treated with a test agent 30 minutes prior to exposure. The degree of retention of ability to form clones after exposure, in comparison to untreated cells, is directly related to the protective effect of the drug. A typical experiment of this type may be carried out essentially as described by Snyder and Lachmann [Radiation Res. 120, 121 (1989)].

Alternatively, the production of DNA strand breaks upon exposure to X-ray dose or chemical dose may be evaluated. Cells are either not drug treated or are treated with a test agent about 30 minutes prior to exposure. The extent of DNA strand breakage after exposure, in comparison to that in untreated cells, is inversely related to the protective effect of the drug. A typical experiment of this type may be carried out essentially as described by Snyder [Int. J. Radiat. Biol. 55, 773 (1989)].

In addition, the survivability of mice exposed to whole body irradiation or to a DNA-reactive agent may be evaluated. Animals, either pre-treated with a test agent or untreated (Control Group), are exposed to whole body irradiation (1500 rads). Untreated Control animals are expected to survive about 12–15 days. The degree of survivability of the treated animals, in comparison to the untreated Controls, is directly related to the protective effect of the drug treatment. A typical experiment of this type may be carried out essentially as described by Carroll et al. [J. Med. Chem. 33, 2501 (1990)].

The production of DNA strand breaks in lymphocytes taken from treated animals exposed to whole body irradiation or to a DNA-reactive agent may be evaluated in comparison to untreated control. Alternatively, the viability and clonogenicity of bone marrow cells taken from treated animals exposed to whole body irradiation or to a DNA-reactive agent may be evaluated in comparison to untreated control as described by Pike and Robinson [J. Cell Physiol. 76, 77 (1970)].

What is claimed is:

1. A compound of the formula

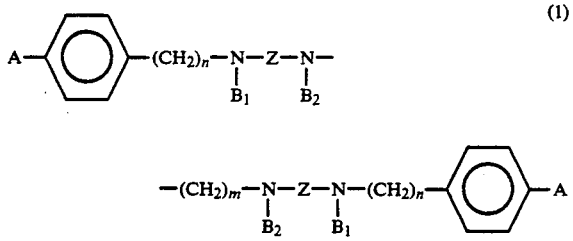

wherein
n is an integer from 0 to 3,
m is an integer from 4 to 9,
Z is a $C_2$-$C_6$ alkylene group,
A is H, $-SH$, $-SPO_3H_2$, $-N(CH_2)_q-SH$, $-N(CH_2)_q-SPO_3H_2$, wherein q is an integer 2 to 4, and
$B_1$ and $B_2$ are each independently H, $-(CH_2)_q-SH$, or $-(CH_2)_q-SPO_3H_2$,
with the proviso that at least one of A, $B_1$ and $B_2$ is other than H.

2. A compound of the formula

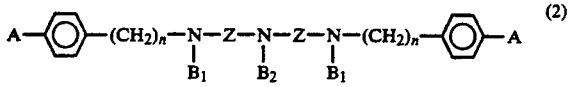

wherein
n is an integer from 0 to 3,
Z is a $C_2$-$C_6$ alkylene group,
A is H, $-SH$, $-SPO_3H_2$, $-N(CH_2)_q-SH$, $-N(CH_2)_q-SPO_3H_2$, wherein q is an integer 2 to 4, and $B_1$ and $B_2$ are each independently H, $-(CH_2)_q-SH$, or $-(CH_2)_q-SPO_3H_2$, with the proviso that at least one of A, $B_1$ and $B_2$ is other than H.

3. A method of protecting mammalian cells from deleterious cellular effects caused by exposure to ionizing radiation comprising contacting said cells with a protective amount of a compound of claim 1 or 2.

4. A method of protecting mammalian cells from deleterious cellular effects caused by exposure to a DNA-reactive agent comprising contacting said cells with a protective amount of a compound of claim 1 or 2.

5. A method of protecting non-cancer cells of a human from deleterious cellular effects caused by exposure to ionizing radiation comprising administering to said human a protective amount of a compound of claim 1 or 2.

6. A method of protecting non-cancer cells of a human from deleterious cellular effects caused by exposure to a DNA-reactive agent comprising administering to said human a protective amount of a compound of claim 1 or 2.

7. A method of treating a patient in need of radiation therapy comprising administering to said patient a protective amount of a compound of claim 1 or 2.

8. A method of treating a patient in need of chemotherapy with a DNA-reactive chemotherapeutic agent comprising administering to said patient a protective amount of a compound of claim 1 or 2.

9. A composition comprising a compound of claim 1 or 2 in admixture or otherwise in association with an inert carrier.

10. A pharmaceutical composition comprising a protective amount of a compound of claim 1 or 2 in admixture or otherwise in association with one or more pharmaceutically acceptable carriers or excipients.

11. A compound of claim 1 wherein n is 1, m is 7 and Z is $-CH_2CH_2CH_2-$.

12. A compound of claim 1 wherein A is H, $-SH$, $-NCH_2CH_2SH$ or $-NCH_2CH_2SPO_3H_2$.

13. A compound of claim 1 wherein $B_1$ and $B_2$ are each H, and A is $-SH$, $-NCH_2CH_2SH$ or $-NCH_2CH_2SPO_3H_2$.

14. A compound of claim 1 wherein $B_1$ and $B_2$ are each $-CH_2CH_2SH$ or $-CH_2CH_2SPO_3H_2$, and A is H.

15. A compound of claim 2 wherein n is 1 and Z is $-CH_2CH_2CH_2-$.

16. A compound of claim 2 wherein A is H, $-SH$, $-NCH_2CH_2SH$ or $-NCH_2CH_2SPO_3H_2$.

17. A compound of claim 2 wherein $B_1$ and $B_2$ are each H, and A is $-SH$, $-NCH_2CH_2SH$ or $-NCH_2CH_2SPO_3H_2$.

18. A compound of claim 2 wherein $B_1$ and $B_2$ are each $-CH_2CH_2SH$ or $-CH_2CH_2SPO_3H_2$, and A is H.

* * * * *

UNITED STATES PATENT AND TRADEMARK OFFICE
CERTIFICATE OF CORRECTION

PATENT NO. : 5,217,964
DATED : June 8, 1993
INVENTOR(S) : Michael L. Edwards et al.

It is certified that error appears in the above-identified patent and that said Letters Patent is hereby corrected as shown below:

At column 2, line 52, the patent reads "-N(CH$_2$)$_q$-SH" and should read -- -NH(CH$_2$)$_q$-SH --.
At column 2, line 53, the patent reads "-N(CH$_2$)$_q$-SPO$_3$H$_2$" and should read -- -NH(CH$_2$)$_q$-SPO$_3$H$_2$ --.
At column 3, line 2, the patent reads "-N(CH$_2$)$_q$-SH" and should read -- -NH(CH$_2$)$_q$-SH --.
At column 3, line 3, the patent reads "-N(CH$_2$)$_q$-SPO$_3$H$_2$" and should read -- -NH(CH$_2$)$_q$-SPO$_3$H$_2$ --.
At column 3, Scheme A, Step C, the patent reads

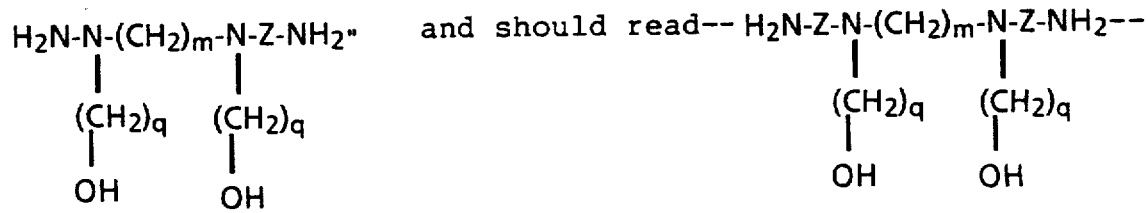

as found in the specification at page 8, Scheme A, Step C.
At column 14, line 8, the patent reads "on vacuo" and should read --in vacuo-- as found in the specification at page 24, line 27.
At column 14, line 19, the patent reads "throught" and should read --through--.
At column 15, Scheme C, the legend reads
"A''' = -SPg, -N(CH$_2$)$_q$-SPg, A" = -SH, -N-(CH$_2$)$_q$-SH, A' = -SPO$_3$H$_2$, -N-(CH$_2$)$_q$-SPO$_3$H$_2$" and should read --A''' = -SPg, -N(HCH$_2$)$_q$-SPg,
A" = -SH, -NH-(CH$_2$)$_q$-SH, A' = -SPO$_3$H$_2$, -NH-(CH$_2$)$_q$-SPO$_3$H$_2$--.
At column 17, lines 38-39, the patent reads "raazanonadecane Dissolve" and should read --raazanonadecane-- (title line) with the word Dissolve appearing at the start of line 40.

UNITED STATES PATENT AND TRADEMARK OFFICE
CERTIFICATE OF CORRECTION

PATENT NO. : 5,217,964
DATED : June 8, 1993
INVENTOR(S) : Michael L. Edwards et al.

Page 2 of 4

It is certified that error appears in the above-identified patent and that said Letters Patent is hereby corrected as shown below:

At column 19, Scheme D, the legend reads "A''' = -SPg, -N(CH$_2$)$_q$-SPg, A" = -SH, -N-(CH$_2$)$_q$-SH, A' = -SPO$_3$H$_2$, -N-(CH$_2$)$_q$-SPO$_3$H$_2$" and should read --A''' = -SPg, -N(HCH$_2$)$_q$-SPg, A" = -SH, -NH-(CH$_2$)$_q$-SH, A' = -SPO$_3$H$_2$, -NH-(CH$_2$)$_q$-SPO$_3$H$_2$--.

At column 25, line 33, the patent reads "Compounds" and should read --compounds--.

At column 27, line 47 and again at column 30, line 1, the patent reads "throught" and should read --through--.

At column 33, line 13, the patent reads "ethanethiolamine 220" and should read --ethanethiolamine--.

At column 33, line 20 and again at column 36, line 38, the patent reads "throught" and should read --through--.

At column 37, Scheme I, the legend reads "A''' = -SPg, -N(CH$_2$)$_q$-SPg, A" = -SH, -N-(CH$_2$)$_q$-SH, A' = -SPO$_3$H$_2$, -N-(CH$_2$)$_q$-SPO$_3$H$_2$" and should read --A''' = -SPg, -N(HCH$_2$)$_q$-SPg, A" = -SH, -NH-(CH$_2$)$_q$-SH, A' = -SPO$_3$H$_2$, -NH-(CH$_2$)$_q$-SPO$_3$H$_2$--.

At column 37, line 37, the patent reads "-2-yl)[-" and should read -- -2-yl)]- --.

At column 38, line 37, the patent reads "trihydrohloride" and shoudl read --trihydrochloride--.

At column 40, line 56, the patent reads "Scheme Scheme B" and should read --Scheme B--..

At column 41, line 5, the patent reads "(CH$_2$)$_9$" and should read --(CH$_2$)$_q$--

At column 41, line 66, the patent reads "(242 mg 9, 4 mmol)" and should read --(242 mg, 4 mmol)--.

At column 41, line 68, the patent reads "throught" and should read --through--.

UNITED STATES PATENT AND TRADEMARK OFFICE
CERTIFICATE OF CORRECTION

PATENT NO. : 5,217,964
DATED : June 8, 1993
INVENTOR(S) : Michael L. Edwards et al.

Page 3 of 4

It is certified that error appears in the above-identified patent and that said Letters Patent is hereby corrected as shown below:

At column 44, Scheme L, the legend reads "A''' = -SPg, -N($CH_2$)$_q$-SPg, A" = -SH, -N-($CH_2$)$_q$-SH, A' = -SPO$_3$H$_2$, -N-($CH_2$)$_q$-SPO$_3$H$_2$" and should read --A''' = -SPg, -N(HCH$_2$)$_q$-SPg, A" = -SH, -NH-($CH_2$)$_q$-SH, A' = -SPO$_3$H$_2$, -NH-($CH_2$)$_q$-SPO$_3$H$_2$--.

At column 44, line 63, the patent reads "the the appropriate" and should read --the appropriate--.

At column 46, line 2, the patent reads "purify be" and should read --purify by--.

At column 46, line 45, the patent reads "1,9-bis(4-" and should read -- 1,9-bis[(4- --.

At column 51, line 39, the patent reads "-NCH$_2$CH$_2$SH or -NCH$_2$CH$_2$SPO$_3$H$_2$" and should read -- -NHCH$_2$CH$_2$SH or -NHCH$_2$CH$_2$SPO$_3$H$_2$ --.

At column 51, line 44, the patent reads "-NCH$_2$CH$_2$SH or -NCH$_2$CH$_2$SPO$_3$H$_2$" and should read -- -NHCH$_2$CH$_2$SH or -NHCH$_2$CH$_2$SPO$_3$H$_2$ --.

At column 51, line 47, the patent reads "-NCH$_2$CH$_2$SH" and should read -- -NHCH$_2$CH$_2$SH --.

At column 51, line 48, the patent reads "-NCH$_2$CH$_2$SPO$_3$H$_2$" and should read -- -NHCH$_2$CH$_2$SPO$_3$H$_2$ --.

At column 51, line 52, the patent reads "-NCH$_2$CH$_2$SH" and should read -- -NHCH$_2$CH$_2$SH --.

At column 51, line 53, the patent reads s "-NCH$_2$CH$_2$SPO$_3$H$_2$" and should read -- -NHCH$_2$CH$_2$SPO$_3$H$_2$ --.

At column 52, line 16, the patent reads "Controls" and should read --controls--.

At column 52, line 49, the patent reads "-N($CH_2$)$_q$-SH" and should read -- -NH($CH_2$)$_q$-SH --.

At column 52, line 50, the patent reads "-N($CH_2$)$_q$-SPO$_3$H$_2$" and should read -- -NH($CH_2$)$_q$-SPO$_3$H$_2$ --.

UNITED STATES PATENT AND TRADEMARK OFFICE
CERTIFICATE OF CORRECTION

PATENT NO.   : 5,217,964
DATED        : June 8, 1993
INVENTOR(S)  : Michael L. Edwards et al.

Page 4 of 4

It is certified that error appears in the above-identified patent and that said Letters Patent is hereby corrected as shown below:

At column 52, line 66, the patent reads "$-N(CH_2)_q-SH$" and should read -- $-NH(CH_2)_q-SH$ --.
At column 52, line 67, the patent reads "$-N(CH_2)_q-SPO_3H_2$" and should read -- $-NH(CH_2)_q-SPO_3H_2$ --.
At column 54, line 13, the patent reads "$-NCH_2CH_2SH$ or $-NCH_2CH_2SPO_3H_2$" and should read -- $-NHCH_2CH_2SH$ or $-NHCH_2CH_2SPO_3H_2$ --.
At column 54, line 15, the patent reads "$-NCH_2CH_2SH$" and should read -- $-NHCH_2CH_2SH$ --.
At column 54, line 16, the patent reads "$-NCH_2CH_2SPO_3H_2$" and should read -- $-NHCH_2CH_2SPO_3H_2$ --.
At column 54, line 22, the patent reads "$-NCH_2CH_2SH$ or $-NCH_2CH_2SPO_3H_2$" and should read -- $-NHCH_2CH_2SH$ or $-NHCH_2CH_2SPO_3H_2$ --.
At column 54, line 24, the patent reads $-NCH_2CH_2SH$" and should read -- $-NHCH_2CH_2SH$ --.
At column 54, line 25, the patent reads "$-NCH_2CH_2SPO_3H_2$" and should read -- $-NHCH_2CH_2SPO_3H_2$ --.

Signed and Sealed this

Ninth Day of May, 1995

Attest:

BRUCE LEHMAN

Attesting Officer

Commissioner of Patents and Trademarks